(12) United States Patent
Makriyannis et al.

(10) Patent No.: US 10,053,444 B2
(45) Date of Patent: *Aug. 21, 2018

(54) CANNABINERGIC NITRATE ESTERS AND RELATED ANALOGS

(71) Applicant: University of Connecticut, Farmington, CT (US)

(72) Inventors: Alexandros Makriyannis, Watertown, MA (US); Kiran Vemuri, Boston, MA (US)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,501

(22) Filed: Oct. 6, 2014

(65) Prior Publication Data

US 2016/0096822 A1 Apr. 7, 2016
US 2017/0001980 A9 Jan. 5, 2017

Related U.S. Application Data

(63) Continuation-in-part of application No. 13/202,499, filed as application No. PCT/US2009/001054 on Feb. 19, 2009, now Pat. No. 8,853,205.

(51) Int. Cl.
C07D 401/12 (2006.01)
C07D 231/14 (2006.01)

(52) U.S. Cl.
CPC ......... *C07D 401/12* (2013.01); *C07D 231/14* (2013.01)

(58) Field of Classification Search
CPC .............................. C07D 401/12; C07D 231/14
See application file for complete search history.

(56) References Cited

U.S. PATENT DOCUMENTS

| | | | |
|---|---|---|---|
| 4,256,727 A | 3/1981 | Triplett et al. | |
| 4,732,900 A | 3/1988 | Weber et al. | |
| 5,155,124 A | 10/1992 | Kimata et al. | |
| 5,208,231 A | 5/1993 | Kimata et al. | |
| 5,462,960 A | 10/1995 | Barth et al. | |
| 5,624,941 A | 4/1997 | Barth et al. | |
| 6,344,474 B1 | 2/2002 | Maruani et al. | |
| 6,432,984 B1 | 8/2002 | Barth et al. | |
| 6,509,367 B1 | 1/2003 | Martin et al. | |
| 7,119,108 B1 | 10/2006 | Makriyannis et al. | |
| 7,393,842 B2 | 7/2008 | Makriyannis et al. | |
| 7,745,440 B2 | 6/2010 | Makriyannis et al. | |
| 7,872,006 B2 | 1/2011 | Moritani et al. | |
| 8,084,451 B2 | 12/2011 | Makriyannis et al. | |
| 8,410,097 B2 | 4/2013 | Makriyannis et al. | |
| 2004/0248956 A1 | 12/2004 | Hagmann et al. | |
| 2007/0117858 A1 | 5/2007 | Xia et al. | |

FOREIGN PATENT DOCUMENTS

| | | | |
|---|---|---|---|
| EP | 0656354 B1 | 6/1997 | |
| WO | 9719063 A1 | 5/1997 | |
| WO | 9721682 A1 | 6/1997 | |
| WO | 2005000820 A3 | 1/2005 | |
| WO | 2006067443 A1 | 6/2006 | |
| WO | WO 2010104488 | * 9/2010 | ............ A01N 43/50 |

OTHER PUBLICATIONS

Ranatunge et al. (J. Med. Chem. 2004, 47, 2180-2193).*
Crocker et al. (Bioorg. Med. Chem. Lett. 17 (2007) 1504-1507).*
Lange et al. (Bioorg. Med. Chem. Lett. 20 (2010) 1752-1757).*
Holla et al. (CAPLUS Abstract of: Indian Journal of Chemistry, Section B: Organic Chemistry Including Medicinal Chemistry (1982), 21B(7), 638-41).*
Kubinyi (3D QSAR in Drug Design: Ligand-Protein Interactions and Molecular Similarity, vol. 2-3, Springer, 1998, 800 pages) p. 243-44 provided.*
Wermuth, The Practice of Medicinal Chemsitry, 2d ed. (2003), 768 pages. Chs. 9-10 provided.*
Fan, H. et al., "Analogs of JHU75528, a PET ligand for imaging of cerebral cannabinoid receptors (CB1): Development of ligands with optimized lipophilicity and binding affinity." European Journal of Medicinal Chemistry, 44, pp. 593-609, 2009.
Howlett, A.C. et al., "Azido- and isothiocyanato-substituted aryl pyrazoles bind covalently to the CB1 cannabinoid receptor and impair signal transduction," Journal of Neurochemistry, Wiley Interscience, New York, NY, US, vol. 74, No. 5, Jan. 1, 2000 (Jan. 1, 2000), 2174-2181.
Lange, J.H.M. et al., "Bioisosteric replacements of the pyrazole moiety of rimonabant: synthesis, biological properties, and molecular modeling investigations of thiazoles, triazoles, and imidazoles as potent and selective CB1 cannabinoid receptor antagonists," Journal of Medicinal Chemistry, American Chemical Society, US, vol. 48, Jan. 1, 2005, 1823-1838.
Jarbe, T. U. et al., "Central mediation and differential blockade by cannabinergics of the discriminative stimulus effects of the cannabinoid CB(1) receptor antagonist rimonabant in rats," Psychopharmacology (Berl). 2011 DOI 10.1007/s00213-011-2226-3).
Cluny, N. L. et al., "The neutral cannabinoid CB receptor antagonist AM4113 regulates body weight through changes in energy intake in the rat," Pharmacol Biochem Behav. 2011, 97, (3), 537-43.

(Continued)

*Primary Examiner* — Robert Havlin
(74) *Attorney, Agent, or Firm* — Alix, Yale & Ristas, LLP

(57) ABSTRACT

Biologically active cannabinergic nitrate esters and related analogs, process of preparation, pharmaceutical compositions and their methods of use as medicaments, pharmacological tools or biomarkers. Pharmaceutical compositions may include one or more of the nitrate ester compounds. Medicaments include one or more of the cannabinergic nitrate ester compounds and are useful in treating a variety of diseases. A method of treating, preventing or reducing the severity of a condition includes administering at least one of the disclosed nitrate ester compounds to an individual or animal in need thereof.

3 Claims, 2 Drawing Sheets

(56) References Cited

OTHER PUBLICATIONS

Randall, P. A. et al., "The novel cannabinoid CB1 antagonist AM6545 suppresses food intake and food-reinforced behavior," Pharmacol Biochem Behav. 2010, 97, (1), 179-84.

Jarbe, T. U. et al., "Intrinsic effects of AM4113, a putative neutral CB1 receptor selective antagonist, on open-field behaviors in rats," Pharmacol Biochem Behav. 2008, 91, (1), 84-90.

Hodge, J. et al., "The cannabinoid CB1 receptor inverse agonist AM 251 and antagonist AM 4113 produce similar effects on the behavioral satiety sequence in rats," Behav Brain Res. 2008, 193, (2), 298-305.

Bergman, J. et al., "Some effects of CB1 antagonists with inverse agonist and neutral biochemical properties," Physiol Behav. 2008, 93, (4-5), 666-70.

Sink, K. S. et al., "Oral bioavailability of the novel cannabinoid CB1 antagonist AM6527: effects on foodreinforced behavior and comparisons with AM4113," Pharmacol Biochem Behav. 2009, 91, (3), 303-6.

Cluny, N. L. et al., "A novel peripherally restricted cannabinoid receptor antagonist, AM6545, reduces food intake and body weight, but does not cause malaise, in rodents," Br J Pharmacol. 2010, 161, (3), 629-42.

Limebeer, C. L. et al., "Inverse agonism of cannabinoid CB1 receptors potentiates LiCl-induced nausea in the conditioned gaping model in rats," Br J Pharmacol. 2010, 161, (2), 336-49.

Tam, J. et al., "Peripheral CB1 cannabinoid receptor blockade improves cardiometabolic risk in mouse models of obesity," J Clin Invest. 2010, 120, (8), 2953-66.

Sink, K. S. et al., "The CB1 inverse agonist AM251, but not the CB1 antagonist AM4113, enhances retention of contextual fear conditioning in rats," Pharmacol Biochem Behav. 2010, 95, (4), 479-84.

Sink, K. S. et al., "Potential anxiogenic effects of cannabinoid CB1 receptor antagonists/inverse agonists in rats: comparisons between AM4113, AM251, and the benzodiazepine inverse agonist FG-7142," Eur. Neuropsychopharmacol. 2010, 20, (2), 112-22.

Storr, M. A. et al., "Differential effects of CB(1) neutral antagonists and inverse agonists on gastrointestinal motility in mice," Neurogastroenterol Motil. 2010, 22, (7), 787-96, e223.

Chambers, A. P. et al., "A neutral CB1 receptor antagonist reduces weight gain in rat," Am J Physiol Regul Integr Comp Physiol. 2007, 293, (6), R2185-93.

Sink, K. S. et al., "The novel cannabinoid CB1 receptor neutral antagonist AM4113 suppresses food intake and food-reinforced behavior but does not induce signs of nausea in rats," Neuropsychopharmacology. 2008, 33, (4), 946-55.

\* cited by examiner

Compound 1    Compound 2

CANNABINERGIC NITRATE ESTERS AND RELATED ANALOGS

STATEMENT REGARDING FEDERALLY SPONSORED RESEARCH OR DEVELOPMENT

This invention was made with Government support under Grant No. DA007215 awarded by the National Institutes of Health. The Government has certain rights in the invention.

BACKGROUND

The present technology generally relates to biologically active novel cannabinergic compounds. In particular, the present technology is related to novel cannabinergic nitrate esters and related analogs.

Marijuana (*Cannabis sativa*) and derivatives have been used for medicinal and recreational purposes. The major active constituent extracted from *Cannabis sativa* is the classical cannabinoid $\Delta^9$-Tetrahydrocannabinol ($\Delta^9$-THC). The effects of such cannabinoids are due to an interaction with specific high-affinity receptors. Subsequently, these discrete mammalian cannabinoid receptors, namely, CB1 and CB2, whose activation by $\Delta^9$-THC elicited psychotropic effects, were cloned. Studies revealed that in humans, CB1 and CB2 share≈44% sequence homology. The CB1 receptor subtype is localized primarily in the central nervous system (CNS), reflecting its prevalence as the most abundant GPCR in brain. CB1 receptors are distributed among the cortex, cerebellum, hippocampus, and basal ganglia, brain regions that control motor, cognitive, emotional, and sensory functions. Hence, central CB1 receptor activation mediates most cannabinoid psychotropic and behavioral effects. The CB1 receptor is also present in high density in the brainstem, hypothalamus, and pituitary gland, loci influencing pain perception; hormonal activity; thermoregulation; and cardiovascular, gastrointestinal, and respiratory physiology. CB1 receptors at peripheral sites (e.g., adipocytes, liver, uterus) help regulate such basic physiological processes as energy balance and reproduction. Although detectable at exceedingly low levels in brain, CB2 receptors are expressed mainly by immune and hematopoietic cells, osteoclasts, and osteoblasts and mediate immune responses, inflammation, inflammatory and neuropathic pain, and bone remodeling.

Virtually all cannabinoid-related medications thus far are related to *Cannabis Sativa*, most of which act as mixed agonists at both CB1 and CB2 receptors. $\Delta^9$-THC (dronabinol, Marinol®) and its synthetic analog, nabilone (Cesamet®) are used as anti-nausea and anti-emetic medications for chemotherapy patients. Nabilone is also approved as an appetite stimulant to treat acquired immune deficiency syndrome-related cachexia. Sativex®, a standardized *Cannabis* extract containing an approximately equal mixture of the two phytocannabinoids ($\Delta^9$-THC and cannabidiol) formulated as a sublingual spray, was initially used for alleviation of neuropathic pain in multiple sclerosis patients and subsequently approved for cancer pain relief.

Rimonabant (SRI 41716A) (Sanofi-Aventis) is a potent CB1-antagonist and its ability to suppress food intake and lower body mass has been demonstrated in humans. Rimonabant's efficacy as a weight-loss agent appeared to involve central, as well as peripheral, mechanisms mediated by the CB1 receptor. As with obesity, studies in appropriate models have shown that CB1-compounds including Rimonabant can decrease the rewarding and psychological/behavioral effects of nicotine, alcohol, and other abused drugs including *cannabis*, opioids, cocaine, heroin, morphine, and methamphetamine. De novo synthetic and high-throughput screening approaches have generated several novel CB1-receptor compounds more structurally distinct from Rimonabant, many of which have been tested in humans (ex. Taranabant, Surinabant, Otenabant, Ibipinabant and Drinabant).

Some of these compounds were radiolabeled and used as molecular probes and in whole body dosimetry studies as well.

SUMMARY OF THE INVENTION

Figure 1:
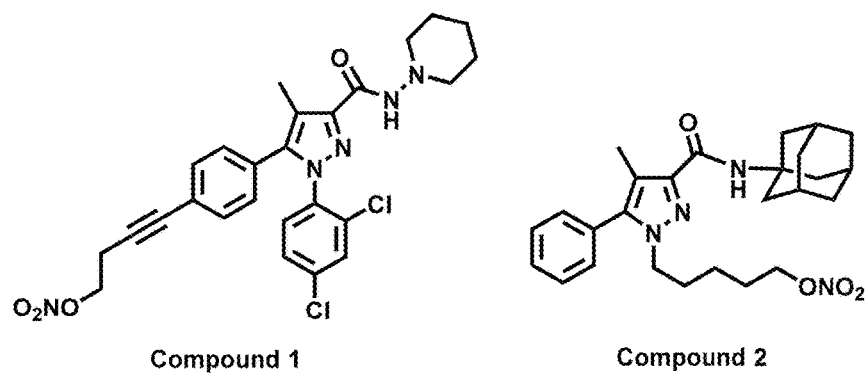
FIG. 1 illustrates chemical structures of Compounds 1 and 2.

Briefly stated, one embodiment of the invention is concerned with new and improved cannabinergic compounds, related analogs, and their pharmaceutical compositions. The inventive ligands of this embodiment can be represented by general formula I and their enantiomers, diastereomers, geometric isomers, racemates, tautomers, rotamers, atropisomers, metabolites, in vivo hydrolyzable esters, N-oxides, salts, solvates, hydrates, polymorphic forms (crystalline or amorphous) or pro-drugs:

V—V1-V2-R—W  (I)

wherein

V is $ONO_2$;

or V is H or is absent when each of V1, V2, R or W independently comprise $ONO_2$;

or V is H or is absent when W is -A-C-B-D and each of A, C, B or D independently comprise $ONO_2$;

V1 if present comprises alkyl, amide, alcohol, ester, heteroalkyl, aryl, heteroaryl, —S-alkyl-, —O-alkyl, —N-alkyl, or —NH-alkyl-;

V2 if present comprises alkyl, amide, alcohol, ester, heteroalkyl, —S-alkyl-, —O—, alkyl, —N-alkyl, —NH-alkyl, —C(O)O—, 0, aryl, heteroaryl, arylalkyl, heteroarylalkyl, arylalkoxy, heteroarylalkoxy, aryloxy or heteroaryloxy;

R comprises aryl, heteroaryl, alkyl or heteroalkyl;

W comprises -A-C-B-D wherein

A if present comprises a direct bond, O, —C(=D1)- or —$(CH_2)_f$N(D2)-;

C if present comprises a direct bond, O, or —C(=O)—;

B if present comprises a direct bond, O, —N(D2)-, —N(D1)(D2)-, —C(D1)(D2)-, —$(CH_2)_f$—, alkyl, aryl, heteroalkyl, heteroarl, alkoxy, aryloxy, heteroarylalkoxy, heteroaryloxy —NH-alkyl-, —$NHSO_2$—:

D1 if present comprises O, S, aryl, ND2, NSO$_2$D2
D2 if present comprises H, C(=NH), OD3, O, alcohol, alkyl, amine, heteroalkyl, aryl, heteroaryl, or SO$_2$alkyl
D3 is H or NO$_2$ and
D if present comprises
a carbocyclic ring, a heterocyclic ring, an aromatic ring, a heteroaromatic ring, a bicyclic ring, a heterobicyclic ring, a tricyclic ring, a heterotricyclic ring, a polycyclic ring or a heteropolycyclic ring; or
D if present comprises

wherein G comprises CH, C(CH$_3$), C(CN) or N;
L, K and J each independently comprise (CH$_2$)$_n$, (CH$_3$)$_2$, C=O, O, —CHOH, C(CH$_3$)OM$_1$, C(CH$_2$)$_n$(X)Y, C(K$_1$)K$_2$, NM$_1$, SO$_2$SO or S;
n is an integer from 0 to about 7;
K$_1$ and K$_2$ are each independently CH$_3$, halogen, OM$_1$, CONM$_1$M$_2$, NM$_1$M$_2$, alkyl, alkylNM$_1$M$_2$, aryl, alcohol, heteroalkyl, heteroaryl
M$_1$ is H, alkyl, SO$_2$(M$_2$), C(O)M$_2$, CONHM$_2$ wherein M$_2$ is H, alkyl, NM$_3$M$_4$, OM$_5$ and M$_3$, M$_4$ and M$_5$ are each independently H, OH, ONO$_2$, alcohol, or alkyl or, and
X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;
X$_1$ and X$_2$ each independently comprise H or alkyl, or
X$_1$ and X$_2$ together comprise part of a heterocyclic ring having about 4 to about 7 ring members and optionally one additional heteroatom selected from O, N or S, or
X$_1$ and X$_2$ together comprise part of an imide ring having about 5 to about 6 members,
X$_3$ comprises H, alkyl, NO$_2$, (CH$_2$)$_m$CN, hydroxylower-alkyl, or alkyl-NX$_1$X$_2$,
X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein
X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein
X$_8$ comprises H, alkyl, carbocyclic ring, heterocyclic ring, aromatic ring, heteroaromatic ring, or —CX$_9$=CHX$_{10}$, wherein
X$_9$ and X$_{10}$ each independently comprise H or alkyl;
m is an integer from 0 to 7;
j is an integer from 0 to about 6; and
k is an integer from 0 to about 2; or
D if present comprises

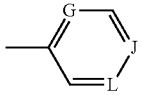

wherein G, L and J each independently comprise CH or N; or
D if present comprises

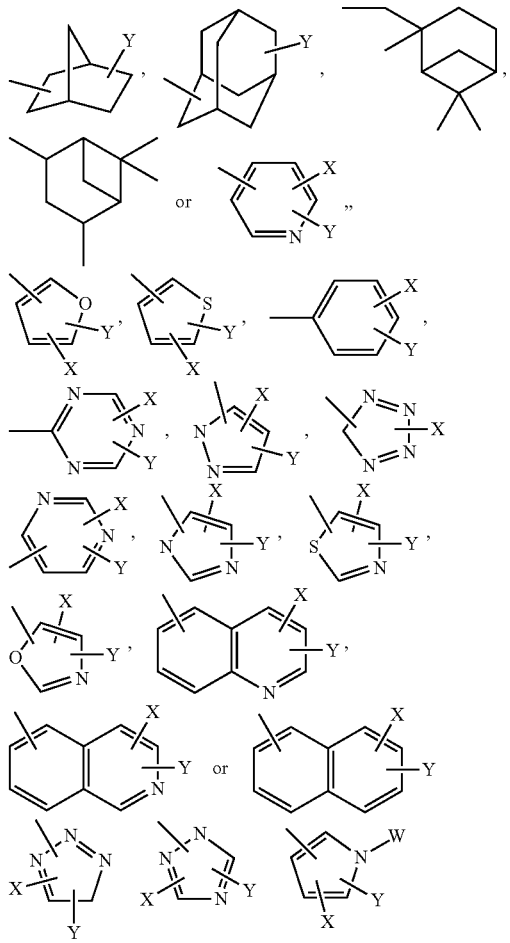

wherein X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;
X$_1$ and X$_2$ each independently comprise H or alkyl, or
X$_1$ and X$_2$ together comprise part of a heterocyclic ring having about 4 to about 7 ring members and optionally one additional heteroatom selected from O, N or S, or
X$_1$ and X$_2$ together comprise part of an imide ring having about 5 to about 6 members,
X$_3$ comprises H, alkyl, NO$_2$, (CH$_2$)$_m$CN, hydroxylower-alkyl, or alkyl-NX$_1$X$_2$,
X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein
X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6;

k is an integer from 0 to about 2; and

W comprises H or alkyl; or

D if present comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, a heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms; or D comprises H, OH, $ONO_2$, alkyl, amide, amine, alcohol or ester Another embodiment of the invention is concerned with new and improved cannabinergic compounds, related analogs, and their pharmaceutical compositions represented by general formula II, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

        V—R—W        (II)

wherein V and W are as defined as in formula I;

R is

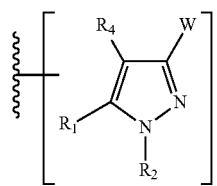

R1 and R2 each independently comprise —$(CH_2)_n$—Z.

n is an integer from 0 to about 7.

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_2OX_3$, $O(CH_2)_j NX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, NO, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, or O-alkyl-$X_7$ wherein $X_7$ comprises H, alkyl, $NO_2$, NO, P(O)$(OX_8)_2$, PH(O)($OX_8$), S(O)$_k$N(alkyl)$_2$, S(O)$_k X_8$, S(O)$_k OX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2

In a variation of R, R1 and R2 each independently comprise —$(CH_2)_n$—Z.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of R, R1 and R2 each independently comprise —$(CH_2)_n$—Z.

n is an integer from 0 to about 7.

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$— group and the Z group can be any available ring carbon atom or any available ring nitrogen atom.

In a variation of R, R1 and R2 each independently comprise —$(CH_2)_n$—Z.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of R, R1 and R2 each independently comprise —(CH$_2$)$_n$—Z.

n is an integer from 0 to about 7.

Z comprises

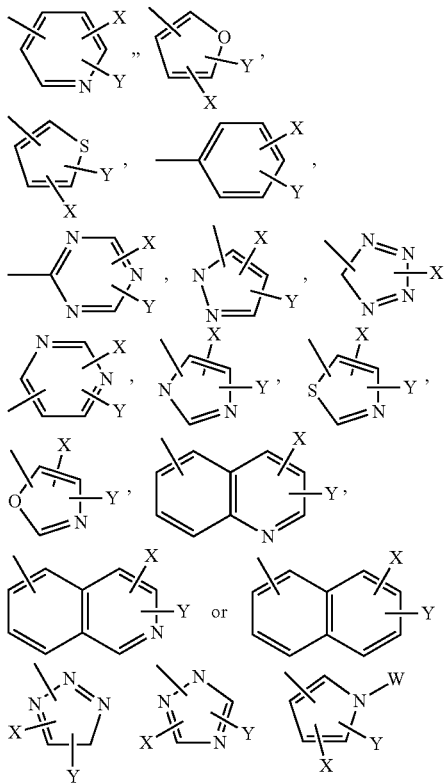

wherein X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$ NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, aryl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl Wherein m is an integer from 0 to 7 j is an integer from 0 to about 6, or

W comprises H or alkyl k is an integer from 0 to about 2

In a variation of R, R1 and R2 each independently —(CH$_2$)$_n$—Z.

n is an integer from 0 to about 7.

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a variation of R, R1 and R2 each independently comprise —(CH$_2$)$_n$—Z;

n comprises an integer from 0 to about 7;

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of R, R1 and R2 each independently comprise —(CH$_2$)$_m$-Q$_1$-(CH$_2$)$_n$—Z;

Q$_1$ comprises NH, O, S, —CH=CH—, —C≡C—, —CO, SO$_2$ or OSO$_2$;

m is an integer from 1 to about 7;

n is an integer from 0 to about 7;

Z comprises H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, O-aroyl, O(CH$_2$)$_j$OX$_3$, O(CH$_2$)$_j$ NX$_1$X$_2$, alkyl-CN, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members;

X$_3$ comprises H, alkyl, NO$_2$, NO, (CH$_2$)$_m$CN, hydroxyloweralkyl, or alkyl-NX$_1$X$_2$;

X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;
m is an integer from 0 to 7;
j is an integer from 0 to about 6, and
k is an integer from 0 to about 2.

In a variation of R, R1 and R2 each independently comprise -$Q_2$-$(CH_2)_n$—Z;

$Q_2$ is optionally present and if present comprises —$CH_2$—NH, —$CH_2$—O, —$CH_2$—S, —$CH_2$—$SO_2$ or —$CH_2$—$OSO_2$;

n is an integer from 0 to about 7;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_jOX_3$, $O(CH_2)_j$ $NX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$ $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, NO, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, P(O)$(OX_8)_2$, PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;
m is an integer from 0 to 7;
j is an integer from 0 to about 6; and
k is an integer from 0 to about 2.

In a variation of R, R1 and R2 each independently comprise —$(CH_2)_m$-$Q_1$-$(CH_2)_n$—Z;

$Q_1$ comprises NH, O, S, CH=CH, C≡C, CO, $SO_2$ or $OSO_2$;
m is an integer from 1 to about 7;
n is an integer from 0 to about 7; and Z comprises a bicyclic ring, a heterobicyclic ring, a tricyclic ring, a heterotricyclic ring, a polycyclic ring or a heteropolycyclic ring.

In a variation of R, R1 and R2 each independently comprise —$(CH_2)_m$-$Q_1$-$(CH_2)_n$—Z;

$Q_1$ comprises NH, O, S, CH=CH, C≡C, CO, $SO_2$ or $OSO_2$;
m is an integer from 1 to about 7;
n is an integer from 0 to about 7;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of R, R1 and R2 each independently comprise —$(CH_2)_m$-$Q_1$-$(CH_2)_n$—Z;

$Q_1$ comprises N, O, S, CH=CH, C≡C, CO, $SO_2$ or $OSO_2$;
m is an integer from 1 to about 7;
n is an integer from 0 to about 7; and Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$— group and the Z group can be any available ring carbon atom or any available ring nitrogen atom.

In a variation of R, R1 and R2 each independently comprise —$(CH_2)_m$-$Q_1$-$(CH_2)_n$—Z;

$Q_1$ comprises NH, O, S, CH=CH, C≡C, CO, $SO_2$ or $OSO_2$;
m is an integer from 1 to about 7;
n is an integer from 0 to about 7; and Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of R, R1 and R2 each independently comprise —$(CH_2)_m$-$Q_1$-$(CH_2)_n$—Z;

$Q_1$ comprises N, O, S, CH=CH, C≡C, CO, $SO_2$ or $OSO_2$;
m is an integer from 1 to about 7;
n is an integer from 0 to about 7;
Z comprises

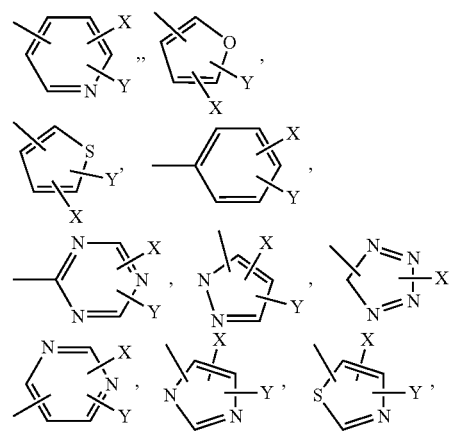

-continued

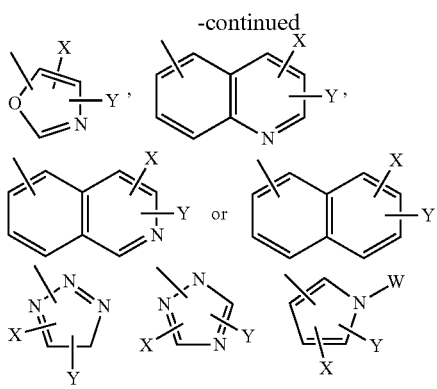

wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_j NX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, $-C\equiv CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or $-CX_9=CHX_{10}$, wherein $X_9$ and $X_{10}$ each independently comprise H or alkyl;
m is an integer from 0 to 7;
j is an integer from 0 to about 6;
k is an integer from 0 to about 2; and
W comprises H or alkyl In a variation of R, R1 and R2 each independently comprise. $-(CH_2)_m$-$Q_1$-$(CH_2)_n$-Z;

$Q_1$ comprises NH, O, S, CH=CH, C≡C, CO, $SO_2$ or $OSO_2$;
m is an integer from 1 to about 7;
n is an integer from 0 to about 7; and
Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of R, R1 and R2 each independently comprise $-(CH_2)_m$-$Q_1$-$(CH_2)_n$-Z;

$Q_1$ comprises NH, O, S, CH=CH, C≡C, CO, $SO_2$ or $OSO_2$;
m is an integer from 1 to about 7;
n is an integer from 0 to about 7; and
Z comprises

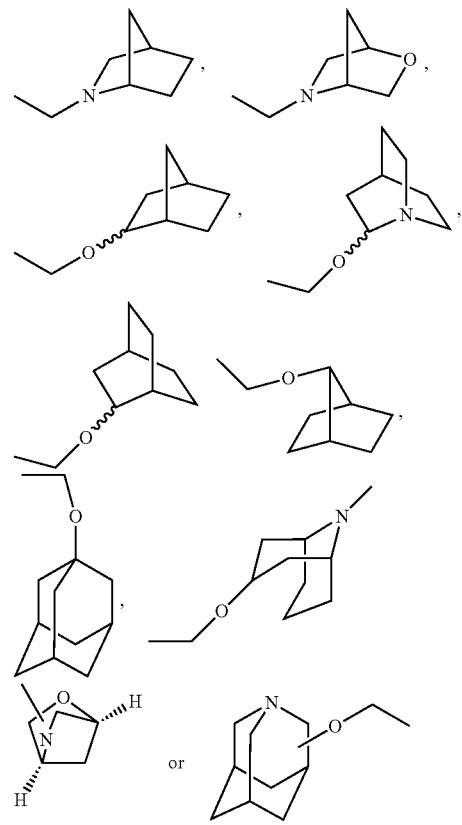

In a variation of R, R1 and R2 each independently comprise -T-$(CH_2)_n$-Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, O-aroyl, $O(CH_2)_jOX_3$, $O(CH_2)_j NX_1X_2$, alkyl-CN, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, $-C\equiv CX_8$ $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, X$_3$ comprises H, alkyl, NO$_2$, NO, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein X$_9$ and X$_{10}$ each independently comprise H or alkyl;

m is an integer from 0 to 7;

j is an integer from 0 to about 6; and k is an integer from 0 to about 2

In a variation of R, R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of R, R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of R, R1 and R2 each independently comprise -T-(CH$_2$)$_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z comprises wherein X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —$CX_9$═$CHX_{10}$ wherein $X_9$ and $X_{10}$ each independently comprise H or alkyl;
m is an integer from 0 to 7;
j is an integer from 0 to about 6;
k is an integer from 0 to about 2; and
W comprises H or alkyl.

In a variation of R, R1 and R2 each independently comprise -T-$(CH_2)_n$—Z;

n comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of R, R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH═CH, C≡C, CO, $SO_2$ or $OSO_2$;

Z comprises H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_jOX_3$, $O(CH_2)_j$ $NX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH═$CHX_8$, —C≡$CX_8$ $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, NO, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, PH(O)($OX_8$), $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$═$CHX_{10}$, wherein $X_9$ and $X_{10}$ each independently comprise H or alkyl;
m is an integer from 0 to 7;
j is an integer from 0 to about 6; and
k is an integer from 0 to about 2

In a variation of R, R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH═CH, C≡C, CO, $SO_2$ or $OSO_2$;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of R, R1 and R2 each independently comprise -T-$(CH_2)_m$-$Q_1$-$(CH_2)_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH═CH, C≡C, CO, $SO_2$ or $OSO_2$;

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of R, R1 and R2 each independently comprise -T-(CH$_2$)$_m$-Q$_1$-(CH$_2$)$_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH=CH, C≡C, CO, SO$_2$ or OSO$_2$;

Z comprises

[chemical structures]

wherein X and Y each independently comprise, H, halogen, CF$_3$, CF$_2$H, N$_3$, NCS, CN, NO$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein X$_9$ and X$_{10}$ each independently comprise H or alkyl;

m is an integer from 0 to 7;

j is an integer from 0 to about 6;

k is an integer from 0 to about 2; and

W comprises H or alkyl.

In a variation of R, R1 and R2 each independently comprise -T-(CH$_2$)$_m$-Q$_1$-(CH$_2$)$_n$—Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH=CH, C≡C, CO, SO$_2$ or OSO$_2$; and

Z comprises an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of R, R1 and R2 each independently comprise -T-(CH$_2$)$_m$-Q$_1$-(CH$_2$)$_n$—Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

m and n independently comprises an integer from 0 to about 7;

Q$_1$ comprises NH, O, S, CH=CH, C≡C, CO, SO$_2$ or OSO$_2$;

Z comprises:

[chemical structures]

wherein E comprises a C1 to about C4, linear or branched alkyl group, a phenyl group, a substituted phenyl group, a benzyl group or a substituted benzyl group.

In a variation of R, R1 and R2 each independently comprise -T-$(CH_2)_m$-$Q_1$-$(CH_2)_n$—Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

m and n independently comprises an integer from 0 to about 7;

$Q_1$ comprises NH, O, S, CH=CH, C≡C, CO, $SO_2$ or $OSO_2$;

Z comprises

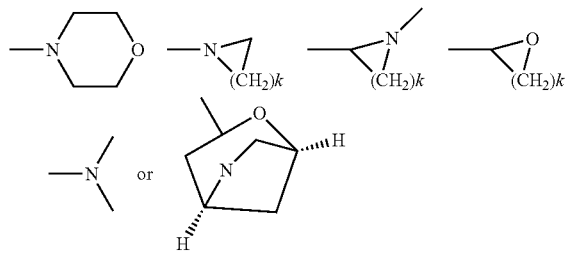

wherein k is an integer from 1 to about 5. $A_1$ and $A_2$ each independently comprise a C1 to about C4 alkyl group, a phenyl group or a substituted phenyl group.

In a variation of R, R4
comprises H, halogen, $CF_3$, $CF_2H$, $N_3$, NCS, CN, $NO_2$, phenyl, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_j OX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$ $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, or O-alkyl-$X_7$, wherein $X_7$ comprises H, alkyl, $NO_2$, NO, P(O)$(OX_8)_2$, PH(O)($OX_8$), S(O)$_k$N(alkyl)$_2$, S(O)$_kX_8$, S(O)$_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of R, R4 comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring or a heteropolycyclic ring.

In an advantageous variation of R, R4 comprises

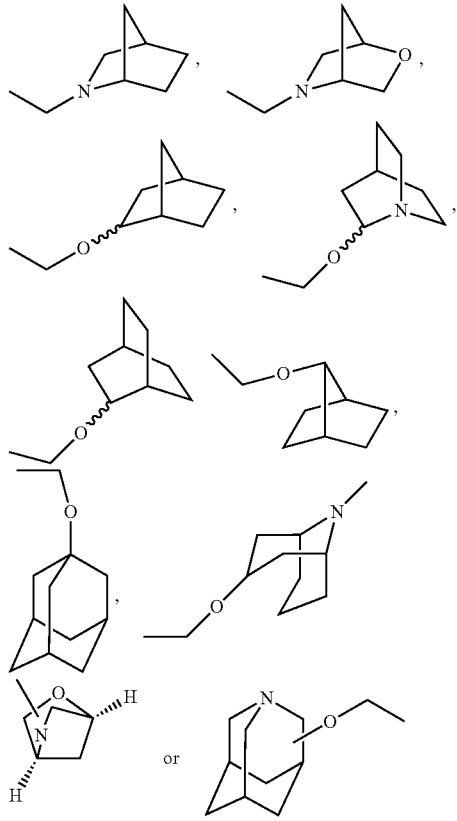

In a variation of R, R4 comprises —$(CH_2)_d$—Z;

d is an integer from 1 to about 6;

comprises H, halogen, $CF_3$, $CF_2H$, $N_3$, NCS, CN, $NO_2$, phenyl, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_j OX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$ $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, or O-alkyl-$X_7$, wherein $X_7$ comprises H, alkyl, $NO_2$, NO, P(O)$(OX_8)_2$, PH(O)($OX_8$), S(O)$_k$N(alkyl)$_2$, S(O)$_kX_8$, S(O)$_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of R, R4 comprises —CH$_2$OH or —CH$_2$Oalkyl.

In a variation of R, R4 comprises —(CH$_2$)$_d$—Z;

d is an integer from 1 to about 6; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom.

In a variation of R, R4 comprises —(CH$_2$)$_d$—Z;

d is an integer from 1 to about 6; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_d$— group and the Z group can be any available ring carbon atom or any available ring nitrogen atom.

In a variation of R, R4 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7;

Z comprises H, halogen, CF$_3$, CF$_2$H, N$_3$, NCS, CN, NO$_2$, phenyl, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$ X$_1$ and X$_2$ each independently comprise H or alkyl, or X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxylower-alkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein X$_9$ and X$_{10}$ each independently comprise H or alkyl;

m is an integer from 0 to 7;

j is an integer from 0 to about 6; and k is an integer from 0 to about 2.

In a variation of R, R4 comprises —(CH$_2$)$_m$-Q$_1$-(CH$_2$)$_n$—Z;

Q$_1$ comprises NH, O, S, CH=CH, C≡C, CO, SO$_2$ or OSO$_2$;

m is an integer from 1 to about 7;

n is an integer from 0 to about 7; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of R R4 comprises —(CH$_2$)$_m$-Q$_1$-(CH$_2$)$_n$—Z.

Q$_1$ comprises NH, O, S, CH=CH, C≡C, CO, SO$_2$ or OSO$_2$.

m is an integer from 1 to about 7.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of R R4 comprises —(CH$_2$)$_m$-Q$_1$-(CH$_2$)$_n$—Z.

Q$_1$ comprises NH, O, S, CH=CH, C≡C, CO, SO$_2$ or OSO$_2$.

m is an integer from 1 to about 7.

n is an integer from 0 to about 7.

Z comprises

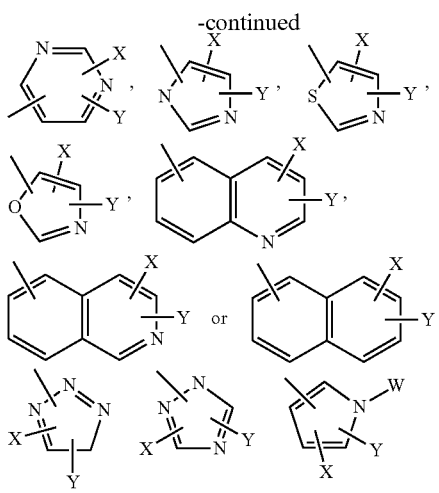

wherein X and Y each independently comprise, H, halogen, $CF_3$, $CF_2H$, $N_3$, NCS, CN, $NO_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_j NX_1X_2$, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl alkoxy, alkyl, alcohol, alkylmercapto, alkylamino, di-alkylamino, alkylsulfinyl or alkylsulfonyl, $CX_4X_5X_6$, $-CH=CHX_8$, $-C\equiv CX_8$;

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxylower-alkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or $-CX_9=CHX_{10}$, wherein $X_9$ and $X_{10}$ each independently comprise H or alkyl;

m is an integer from 0 to 7;

j is an integer from 0 to about 6;

k is an integer from 0 to about 2;

W comprises H or alkyl; and

V if present is attached to any part of R via a covalent bond.

Another embodiment of the invention is concerned with new and improved cannabinergic compounds, related analogs, and their pharmaceutical compositions represented by general formula III, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

V—R—W  (III)

wherein V and W are as defined as in formula I;
R is

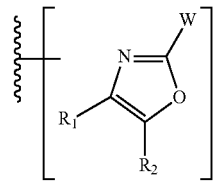

and R1, R2 are as defined above for compounds of R;
V if present is attached to any part of R via a covalent bond.

Another embodiment of the invention is concerned with new and improved cannabinergic compounds, related analogs, and their pharmaceutical compositions represented by general formula IV, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

V—R—W  (IV)

wherein V and W are as defined as in formula I;
R is

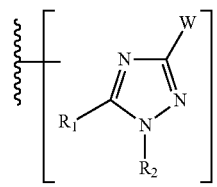

and R1, R2 are as defined above for compounds of R.
V if present is attached to any part of R via a covalent bond.

Another embodiment of the invention is concerned with new and improved cannabinergic compounds, related analogs, and their pharmaceutical compositions represented by general formula V, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

V—R—W  (V)

wherein V and W are as defined as in formula I;
R is

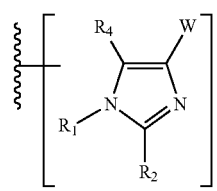

and R1, R2 and R4 are as defined above for compounds of R.
V if present is attached to any part of R via a covalent bond.

Another embodiment of the invention is concerned with new and improved cannabinergic compounds, related analogs, and their pharmaceutical compositions represented by general formula VI, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

wherein V and W are as defined as in formula I;
R is

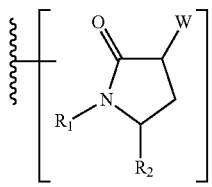

and R1, R2 are as defined above for compounds of R.
V if present is attached to any part of R via a covalent bond.

Another embodiment of the invention is concerned with new and improved cannabinergic compounds, related analogs, and their pharmaceutical compositions represented by general formula VII, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

wherein V and W are as defined as in formula I;
R is

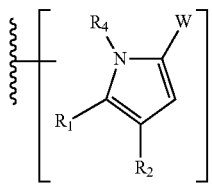

and R1, R2, R4 are as defined above for compounds of R.
V if present is attached to any part of R via a covalent bond.

Another embodiment of the invention is concerned with new and improved cannabinergic compounds, related analogs, and their pharmaceutical compositions represented by general formula VIII, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

wherein V and W are as defined as in formula I;
R is

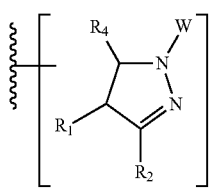

and R1, R2, R4 are as defined above for compounds of R.
V if present is attached to any part of R via a covalent bond.

Another embodiment of the invention is concerned with new and improved cannabinergic compounds, related analogs, and their pharmaceutical compositions represented by general formula IX, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

wherein V and W are as defined as in formula I;
R is

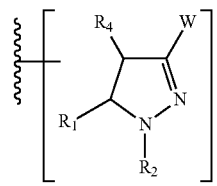

and R1, R2, R4 are as defined above for compounds of R.
V if present is attached to any part of R via a covalent bond.

Another embodiment of the invention is concerned with new and improved cannabinergic compounds, related analogs, and their pharmaceutical compositions represented by general formula X, and their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

wherein V and W are as defined as in formula I;
R is

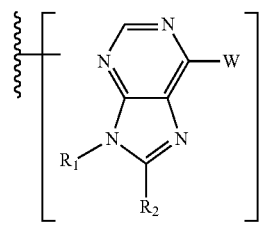

and R1, R2 are as defined above for compounds of R.
V if present is attached to any part of R via a covalent bond.

Another embodiment of the invention is concerned with new and improved cannabinergic compounds, related analogs, and their pharmaceutical compositions represented by general formula XI, and their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

wherein V and W are as defined as in formula I;
R is

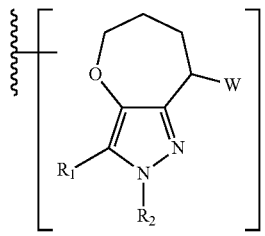

and R1, R2 are as defined above for compounds of R.

V if present is attached to any part of R via a covalent bond.

Another embodiment of the invention is concerned with new and improved cannabinergic compounds, related analogs, and their pharmaceutical compositions represented by general formula XII, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

 (XII)

wherein V and W are as defined as in formula I;
R is

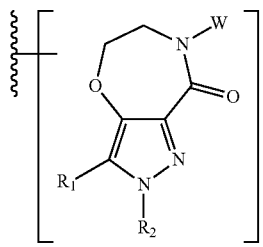

and R1, R2 are as defined above for compounds of R.

V if present is attached to any part of R via a covalent bond.

Another embodiment of the invention is concerned with new and improved cannabinergic compounds, related analogs, and their pharmaceutical compositions represented by general formula XIII, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

 (XIII)

wherein V and W are as defined as in formula I;
R is

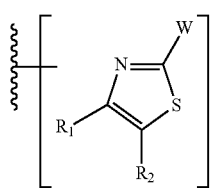

and R1, R2 are as defined above for compounds of R.

V if present is attached to any part of R via a covalent bond.

Another embodiment of the invention is concerned with new and improved cannabinergic compounds, related analogs, and their pharmaceutical compositions represented by general formula XIV, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

 (XIV)

wherein V and W are as defined as in formula I;
R is

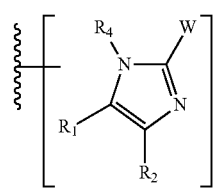

and R1, R2 are as defined above for compounds of R.

V if present is attached to any part of R via a covalent bond.

Another embodiment of the invention is concerned with new and improved cannabinergic compounds, related analogs, and their pharmaceutical compositions represented by general formula XV, their enantiomers, diastereomers, geometric isomers, racemates, tautomers, rotamers, atropisomers, metabolites, in vivo hydrolysable esters, N-oxides, salts, solvates, hydrates, polymorphic forms (crystalline or amorphous) or pro-drugs:

 (XV)

wherein V and W are as defined as in formula I;
R is

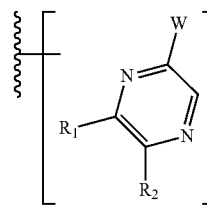

and R1, R2 are as defined above for compounds of R.

V if present is attached to any part of R via a covalent bond.

Some embodiments of the invention is concerned with new and improved cannabinergic compounds, related analogs, and their pharmaceutical compositions of formula I-XV, wherein W is -A-C-B-D wherein A comprises a direct bond, O, or $-(CH_2)_f N(D2)-$;

C is $C(=O)$

B comprises a direct bond, O, N(D2), $-(CH_2)_f-$ or $-NH-SO_2-$

D2 is hydrogen, OH, alkyl or substituted alkyl and

I is an integer from 0 to 3;

Some embodiments of the invention is concerned with new and improved cannabinergic compounds, related analogs, and their pharmaceutical compositions represented by general formula XVI:

R—W  (XVI)

R is

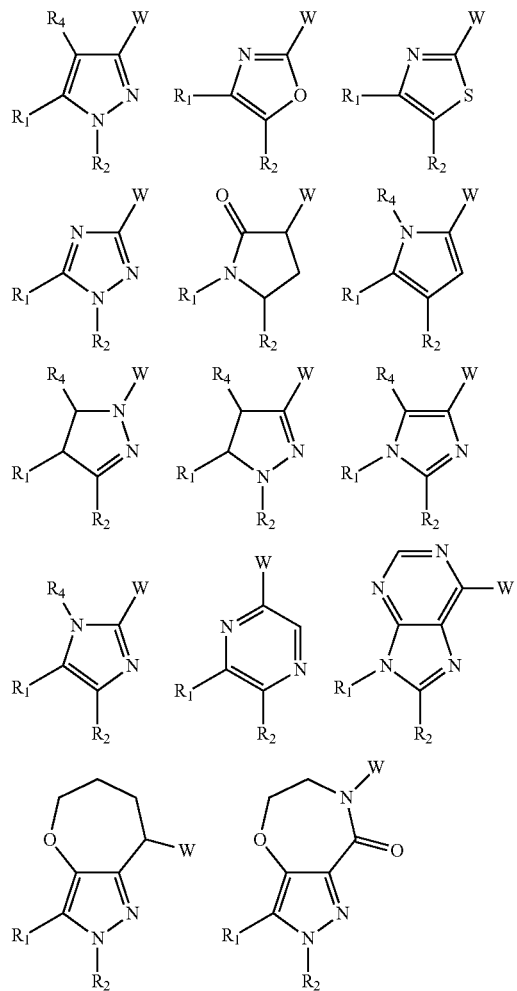

R1, R2, R4 and W are as defined above for compounds of formula I and

R and each of R1, R2, R4 or W independently comprise at least one group comprising ONO2

Some embodiments of the invention is concerned with new and improved cannabinergic compounds, related analogs, and their pharmaceutical compositions represented by general formula I wherein V is ONO2

V1 is alkyl

V2 is aryl or heteroaryl

R is

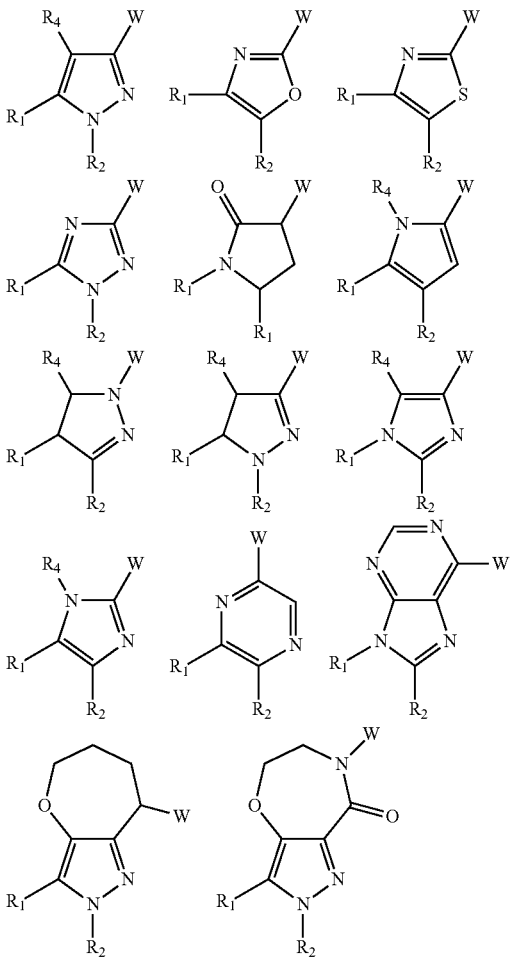

A is a direct bond

C is C(=O)

B is NH

Some embodiments of the invention is concerned with new and improved cannabinergic compounds, related analogs, and their pharmaceutical compositions represented by general formula I wherein V is ONO2

V1 is alkyl

V2 is aryl or heteroaryl

R is heteroalkyl

Some embodiments of the invention is concerned with new and improved cannabinergic compounds, related analogs, and their pharmaceutical compositions represented by general formula I wherein V is $ONO_2$ V1 is alkyl V2 is aryl or heteroaryl R is heteroalkyl B is —N(D1)(D2)

Some embodiments of the invention is concerned with new and improved cannabinergic compounds, related analogs, and their pharmaceutical compositions represented by general formula I wherein V is ONO2

V1 is alkyl

R is heteroaryl

Some embodiments of the invention is concerned with new and improved cannabinergic compounds, related analogs, and their pharmaceutical compositions represented by general formula I wherein
V is ONO2
V1 is alkyl
C is C(=O)
B is —N(D1)(D2)
Some embodiments of the invention is concerned with new and improved cannabinergic compounds, related analogs, and their pharmaceutical compositions represented by general formula I wherein
V is ONO2
V1 is alkyl
B is —C(D1)(D2)
In some embodiments, the compounds of the general formula I include: 4-(4-(1-(2,4-dichlorophenyl)-4-methyl-3-(piperidin-1-ylcarbamoyl)-1H-pyrazol-5-yl)phenyl)but-3-yn-1-yl nitrate; 4-(4-(1-(2,4-dichlorophenyl)-4-methyl-3-(morpholinocarbamoyl)-1H-pyrazol-5-yl)phenyl)but-3-yn-1-yl nitrate; 5-(4-(1-(2,4-dichlorophenyl)-3-((1,1-dioxidothiomorpholino)carbamoyl)-4-methyl-1H-pyrazol-5-yl)phenyl)pent-4-yn-1-yl nitrate; 4-(4-(3-((1-cyanocyclopropyl)carbamoyl)-1-(2,4-dichlorophenyl)-4-methyl-1H-pyrazol-5-yl)phenyl)but-3-yn-1-yl nitrate; 5-(4-(1-(2,4-dichlorophenyl)-3-((1,1-dioxidothiomorpholino)carbamoyl)-4-methyl-1H-pyrazol-5-yl)phenyl)pent-4-yn-1-yl nitrate; 4-(4-(1-(2,4-dichlorophenyl)-4-methoxy-3-(piperidin-1-ylcarbamoyl)-1H-pyrazol-5-yl)phenyl)but-3-yn-1-yl nitrate; 4-(4-(1-(2,4-dichlorophenyl)-4-methoxy-3-(morpholinocarbamoyl)-1H-pyrazol-5-yl)phenyl)but-3-yn-1-yl nitrate; 4-(4-(1-(2,4-dichlorophenyl)-3-((1,1-dioxidothiomorpholino)carbamoyl)-4-methoxy-1H-pyrazol-5-yl)phenyl)but-3-yn-1-yl nitrate; 4-(4-(3-((1-cyanocyclopropyl)carbamoyl)-1-(2,4-dichlorophenyl)-4-methoxy-1H-pyrazol-5-yl)phenyl)but-3-yn-1-yl nitrate; 4-(4-(1-(2,4-dichlorophenyl)-3-((1,1-dioxidotetrahydro-2H-thiopyran-4-yl)carbamoyl)-4-methoxy-1H-pyrazol-5-yl)phenyl)but-3-yn-1-yl nitrate; 4-(4-(3-(cyclohexylcarbamoyl)-1-(2,4-dichlorophenyl)-4-methoxy-1H-pyrazol-5-yl)phenyl)but-3-yn-1-yl nitrate; 4-(4-(1-(2,4-dichlorophenyl)-4-methoxy-3-(piperidine-1-carbonyl)-1H-pyrazol-5-yl)phenyl)but-3-yn-1-yl nitrate; 4-(4-(1-(2,4-dichlorophenyl)-3-((4,4-difluoropiperidin-1-yl)carbamoyl)-4-methoxy-1H-pyrazol-5-yl)phenyl)but-3-yn-1-yl nitrate; 4-(4-(1-(2,4-dichlorophenyl)-4-methoxy-3-((2-oxotetrahydro-2H-pyran-3-yl)carbamoyl)-1H-pyrazol-5-yl)phenyl)but-3-yn-1-yl nitrate 4-(4-(1-(2,4-dichlorophenyl)-3-((hexahydrocyclopenta[c]pyrrol-2(1H)-yl)carbamoyl)-4-methyl-1H-pyrazol-5-yl)phenyl)but-3-yn-1-yl nitrate; 1-(5-(4-bromophenyl)-1-(2,4-dichlorophenyl)-4-ethyl-1H-pyrazole-3-carboxamido)piperidin-4-yl nitrate; 1-(5-(4-bromophenyl)-1-(2,4-dichlorophenyl)-4-methoxy-1H-pyrazole-3-carboxamido)piperidin-4-yl nitrate; 1-(5-(4-(4-cyanobut-1-yn-1-yl)phenyl)-1-(2,4-dichlorophenyl)-4-ethyl-1H-pyrazole-3-carboxamido)piperidin-4-yl nitrate; 1-(5-(4-(4-cyanobut-1-yn-1-yl)phenyl)-1-(2,4-dichlorophenyl)-4-methoxy-1H-pyrazole-3-carboxamido)piperidin-4-yl nitrate; 4-(5-(1-(2,4-dichlorophenyl)-4-methyl-3-(piperidin-1-ylcarbamoyl)-1H-pyrazol-5-yl)thiophen-2-yl)but-3-yn-1-yl nitrate; 4-(5-(1-(2,4-dichlorophenyl)-4-methyl-3-(morpholinocarbamoyl)-1H-pyrazol-5-yl)thiophen-2-yl)but-3-yn-1-yl nitrate; 4-(5-(3-((1-cyanocyclopropyl)carbamoyl)-1-(2,4-dichlorophenyl)-4-methyl-1H-pyrazol-5-yl)thiophen-2-yl)but-3-yn-1-yl nitrate; 4-(5-(1-(2,4-dichlorophenyl)-3-((1,1-dioxidothiomorpholino)carbamoyl)-4-methyl-1H-pyrazol-5-yl)thiophen-2-yl)but-3-yn-1-yl nitrate; 4-(5-(1-(2,4-dichlorophenyl)-4-methoxy-3-(morpholinocarbamoyl)-1H-pyrazol-5-yl)thiophen-2-yl)but-3-yn-1-yl nitrate; 4-(5-(1-(2,4-dichlorophenyl)-4-methoxy-3-(piperidin-1-ylcarbamoyl)-1H-pyrazol-5-yl)thiophen-2-yl)but-3-yn-1-yl nitrate; 4-(5-(1-(2,4-dichlorophenyl)-3-((1,1-dioxidothiomorpholino)carbamoyl)-4-methoxy-1H-pyrazol-5-yl)thiophen-2-yl)but-3-yn-1-yl nitrate; 4-(5-(3-((1-cyanocyclopropyl)carbamoyl)-1-(2,4-dichlorophenyl)-4-methoxy-1H-pyrazol-5-yl)thiophen-2-yl)but-3-yn-1-yl nitrate; 1-(5-(5-bromothiophen-2-yl)-1-(2,4-dichlorophenyl)-4-ethyl-1H-pyrazole-3-carboxamido)piperidin-4-yl nitrate; 1-(5-(5-bromothiophen-2-yl)-1-(2,4-dichlorophenyl)-4-methoxy-1H-pyrazole-3-carboxamido)piperidin-4-yl nitrate; 1-(5-(5-(4-cyanobut-1-yn-1-yl)thiophen-2-yl)-1-(2,4-dichlorophenyl)-4-ethyl-1H-pyrazole-3-carboxamido)piperidin-4-yl nitrate; 1-(5-(5-(4-cyanobut-1-yn-1-yl)thiophen-2-yl)-1-(2,4-dichlorophenyl)-4-methoxy-1H-pyrazole-3-carboxamido)piperidin-4-yl nitrate; 2-(nitrooxy)ethyl 2-(4-(1-(2,4-dichlorophenyl)-4-methyl-3-(piperidin-1-ylcarbamoyl)-1H-pyrazol-5-yl)phenyl)-2-methylpropanoate; propyl 2-(4-(1-(2,4-dichlorophenyl)-4-methyl-3-((4-(nitrooxy)piperidin-1-yl)carbamoyl)-1H-pyrazol-5-yl)phenyl)-2-methylpropanoate; 4-(4-(1-(2-chloro-4-fluorophenyl)-4-methyl-3-(piperidin-1-ylcarbamoyl)-1H-pyrazol-5-yl)phenyl)but-3-yn-1-yl nitrate; 4-(4-(1-(2-chloro-4-fluorophenyl)-4-methyl-3-(morpholinocarbamoyl)-1H-pyrazol-5-yl)phenyl)but-3-yn-1-yl nitrate; 4-(4-(1-(2-chloro-4-fluorophenyl)-3-((1,1-dioxidothiomorpholino)carbamoyl)-4-methyl-1H-pyrazol-5-yl)phenyl)but-3-yn-1-yl nitrate; 4-(4-(1-(2-chloro-4-fluorophenyl)-3-((1,1-dioxidothiomorpholino)carbamoyl)-4-methoxy-1H-pyrazol-5-yl)phenyl)but-3-yn-1-yl nitrate; 1-(tert-butoxycarbonyl)azetidin-3-yl 1-(2,4-dichlorophenyl)-4-methyl-5-(4-(4-(nitrooxy)but-1-yn-1-yl)phenyl)-1H-pyrazole-3-carboxylate; 1-ethynylcyclohexyl 1-(2,4-dichlorophenyl)-4-methyl-5-(4-(4-(nitrooxy)but-1-yn-1-yl)phenyl)-1H-pyrazole-3-carboxylate; azetidin-3-yl 1-(2,4-dichlorophenyl)-4-methyl-5-(4-(4-(nitrooxy)but-1-yn-1-yl)phenyl)-1H-pyrazole-3-carboxylate 2,2,2-trifluoroacetate; 1-(2,4-dichlorophenyl)-4-methyl-3-(piperidin-1-ylcarbamoyl)-1H-pyrazol-5-yl 4-(4-cyanobut-1-yn-1-yl)benzoate 1-(2,4-dichlorophenyl)-4-methyl-3-((4-(nitrooxy)piperidin-1-yl)carbamoyl)-1H-pyrazol-5-yl 4-chlorobenzoate; 5-(3-(((3s,5s,7s)-adamantan-1-yl)carbamoyl)-4-methyl-5-phenyl-1H-pyrazol-1-yl)pentyl nitrate; 6-(3-(((3s,5s,7s)-adamantan-1-yl)carbamoyl)-4-methyl-5-phenyl-1H-pyrazol-1-yl)hexyl nitrate; 5-(3-((1-cyanocyclopropyl)carbamoyl)-4-methyl-5-phenyl-1H-pyrazol-1-yl)pentyl nitrate; 5-(3-((1,1-dioxidotetrahydro-2H-thiopyran-4-yl)carbamoyl)-4-methyl-5-phenyl-1H-pyrazol-1-yl)pentyl nitrate; 5-(3-((1,1-dioxidothiomorpholino)carbamoyl)-4-methyl-5-phenyl-1H-pyrazol-1-yl)pentyl nitrate; 4-(4-(3-(((3s,5s,7s)-adamantan-1-yl)carbamoyl)-1-(1,1-dioxidotetrahydrothiophen-3-yl)-4-methyl-1H-pyrazol-5-yl)phenyl)but-3-yn-1-yl nitrate; 4-(4-methyl-1-pentyl-5-phenyl-1H-pyrazole-3-carboxamido)cyclohexyl nitrate; 4-(4-(3-((1-cyanocyclopropyl)carbamoyl)-1-(1,1-dioxidotetrahydrothiophen-3-yl)-4-methyl-1H-pyrazol-5-yl)phenyl)but-3-yn-1-yl nitrate; 4-(4-(2-(2,4-dichlorophenyl)-5-methyl-4-(piperidin-1-ylcarbamoyl)-1H-imidazol-1-yl)phenyl)but-3-yn-1-yl nitrate; 4-(4-(2-(2,4-dichlorophenyl)-5-methyl-4-(morpholinocarbamoyl)-1H-imidazol-1-yl)phenyl)but-3-yn-1-yl nitrate; 4-(4-(4-((1-cyanocyclopropyl)carbamoyl)-2-(2,4-dichlorophenyl)-5-methyl-1H-imidazol-1-yl)phenyl)but-3-yn-1-yl nitrate; 5-(4-(2-(2,4-dichlorophenyl)-4-((1,1-dioxidothiomorpholino)carbamoyl)-5-methyl-1H-imidazol-1-yl)

phenyl)pent-4-yn-1-yl nitrate; 4-(4-(2-(2,4-dichlorophenyl)-5-methoxy-4-(morpholinocarbamoyl)-1H-imidazol-1-yl)phenyl)but-3-yn-1-yl nitrate; 4-(4-(2-(2,4-dichlorophenyl)-5-methoxy-4-(piperidin-1-ylcarbamoyl)-1H-imidazol-1-yl)phenyl)but-3-yn-1-yl nitrate; 4-(4-(2-(2,4-dichlorophenyl)-4-((1,1-dioxidothiomorpholino)carbamoyl)-5-methoxy-1H-imidazol-1-yl)phenyl)but-3-yn-1-yl nitrate; 4-(4-(4-((1-cyanocyclopropyl)carbamoyl)-2-(2,4-dichlorophenyl)-5-methoxy-1H-imidazol-1-yl)phenyl)but-3-yn-1-yl nitrate; 4-(4-(2-(2,4-dichlorophenyl)-4-((hexahydrocyclopenta[c]pyrrol-2(1H)-yl)carbamoyl)-5-methyl-1H-imidazol-1-yl)phenyl)but-3-yn-1-yl nitrate; 4-(4-(4-(cyclohexylcarbamoyl)-2-(2,4-dichlorophenyl)-5-methoxy-1H-imidazol-1-yl)phenyl)but-3-yn-1-yl nitrate; 4-(4-(2-(2,4-dichlorophenyl)-5-methoxy-4-(piperidine-1-carbonyl)-1H-imidazol-1-yl)phenyl)but-3-yn-1-yl nitrate; 4-(4-(2-(2,4-dichlorophenyl)-4-((4,4-difluoropiperidin-1-yl)carbamoyl)-5-methoxy-1H-imidazol-1-yl)phenyl)but-3-yn-1-yl nitrate; 4-(4-(2-(2,4-dichlorophenyl)-4-((1,1-dioxidotetrahydro-2H-thiopyran-4-yl)carbamoyl)-5-methoxy-1H-imidazol-1-yl)phenyl)but-3-yn-1-yl nitrate; 4-(4-(2-(2,4-dichlorophenyl)-5-methoxy-4-((2-oxotetrahydro-2H-pyran-3-yl)carbamoyl)-1H-imidazol-1-yl)phenyl)but-3-yn-1-yl nitrate; 1-(1-(4-bromophenyl)-2-(2,4-dichlorophenyl)-5-ethyl-1H-imidazole-4-carboxamido)piperidin-4-yl nitrate; 1-(1-(4-bromophenyl)-2-(2,4-dichlorophenyl)-5-methoxy-1H-imidazole-4-carboxamido)piperidin-4-yl nitrate; 1-(1-(4-(4-cyanobut-1-yn-1-yl)phenyl)-2-(2,4-dichlorophenyl)-5-ethyl-1H-imidazole-4-carboxamido)piperidin-4-yl nitrate; 1-(1-(4-(4-cyanobut-1-yn-1-yl)phenyl)-2-(2,4-dichlorophenyl)-5-methoxy-1H-imidazole-4-carboxamido)piperidin-4-yl nitrate; 4-(5-(2-(2,4-dichlorophenyl)-5-methyl-4-(piperidin-1-ylcarbamoyl)-1H-imidazol-1-yl)thiophen-2-yl)but-3-yn-1-yl nitrate; 4-(5-(2-(2,4-dichlorophenyl)-5-methyl-4-(morpholinocarbamoyl)-1H-imidazol-1-yl)thiophen-2-yl)but-3-yn-1-yl nitrate; 4-(5-(4-((1-cyanocyclopropyl)carbamoyl)-2-(2,4-dichlorophenyl)-5-methyl-1H-imidazol-1-yl)thiophen-2-yl)but-3-yn-1-yl nitrate; 4-(5-(2-(2,4-dichlorophenyl)-4-((1,1-dioxidothiomorpholino)carbamoyl)-5-methyl-1H-imidazol-1-yl)thiophen-2-yl)but-3-yn-1-yl nitrate; 4-(5-(2-(2,4-dichlorophenyl)-5-methoxy-4-(morpholinocarbamoyl)-1H-imidazol-1-yl)thiophen-2-yl)but-3-yn-1-yl nitrate; 4-(5-(2-(2,4-dichlorophenyl)-5-methoxy-4-(piperidin-1-ylcarbamoyl)-1H-imidazol-1-yl)thiophen-2-yl)but-3-yn-1-yl nitrate; 4-(5-(2-(2,4-dichlorophenyl)-4-((1,1-dioxidothiomorpholino)carbamoyl)-5-methoxy-1H-imidazol-1-yl)thiophen-2-yl)but-3-yn-1-yl nitrate; 4-(5-(4-((1-cyanocyclopropyl)carbamoyl)-2-(2,4-dichlorophenyl)-5-methoxy-1H-imidazol-1-yl)thiophen-2-yl)but-3-yn-1-yl nitrate; 1-(1-(5-bromothiophen-2-yl)-2-(2,4-dichlorophenyl)-5-ethyl-1H-imidazole-4-carboxamido)piperidin-4-yl nitrate; 1-(1-(5-bromothiophen-2-yl)-2-(2,4-dichlorophenyl)-5-methoxy-1H-imidazole-4-carboxamido)piperidin-4-yl nitrate; 4-(4-(4-(2,4-dichlorophenyl)-1-methyl-2-(piperidin-1-ylcarbamoyl)-1H-imidazol-5-yl)phenyl)but-3-yn-1-yl nitrate; 4-(4-(4-(2,4-dichlorophenyl)-1-methyl-2-(morpholinocarbamoyl)-1H-imidazol-5-yl)phenyl)but-3-yn-1-yl nitrate; 5-(4-(4-(2,4-dichlorophenyl)-2-((1,1-dioxidothiomorpholino)carbamoyl)-1-methyl-1H-imidazol-5-yl)phenyl)pent-4-yn-1-yl nitrate; 4-(4-(2-((1-cyanocyclopropyl)carbamoyl)-4-(2,4-dichlorophenyl)-1-methyl-1H-imidazol-5-yl)phenyl)but-3-yn-1-yl nitrate; 1-(1-(5-(4-cyanobut-1-yn-1-yl)thiophen-2-yl)-2-(2,4-dichlorophenyl)-5-ethyl-1H-imidazole-4-carboxamido)piperidin-4-yl nitrate; 1-(1-(5-(4-cyanobut-1-yn-1-yl)thiophen-2-yl)-2-(2,4-dichlorophenyl)-5-methoxy-1H-imidazole-4-carboxamido)piperidin-4-yl nitrate; propyl 2-(4-(2-(2,4-dichlorophenyl)-5-methyl-4-((4-(nitrooxy)piperidin-1-yl)carbamoyl)-1H-imidazol-1-yl)phenyl)-2-methylpropanoate; 4-(4-(2-(2-chloro-4-fluorophenyl)-5-methyl-4-(piperidin-1-ylcarbamoyl)-1H-imidazol-1-yl)phenyl)but-3-yn-1-yl nitrate; 4-(4-(2-(2-chloro-4-fluorophenyl)-5-methyl-4-(morpholinocarbamoyl)-1H-imidazol-1-yl)phenyl)but-3-yn-1-yl nitrate; 4-(4-(2-(2-chloro-4-fluorophenyl)-4-((1,1-dioxidothiomorpholino)carbamoyl)-5-methyl-1H-imidazol-1-yl)phenyl)but-3-yn-1-yl nitrate; 4-(4-(2-(2-chloro-4-fluorophenyl)-4-((1,1-dioxidothiomorpholino)carbamoyl)-5-methoxy-1H-imidazol-1-yl)phenyl)but-3-yn-1-yl nitrate; azetidin-3-yl 2-(2,4-dichlorophenyl)-5-methyl-1-(4-(4-(nitrooxy)but-1-yn-1-yl)phenyl)-1H-imidazole-4-carboxylate 2,2,2-trifluoroacetate; 1-ethynylcyclohexyl 2-(2,4-dichlorophenyl)-5-methyl-1-(4-(4-(nitrooxy)but-1-yn-1-yl)phenyl)-1H-imidazole-4-carboxylate 1-(tert-butoxycarbonyl)azetidin-3-yl 2-(2,4-dichlorophenyl)-5-methyl-1-(4-(4-(nitrooxy)but-1-yn-1-yl)phenyl)-1H-imidazole-4-carboxylate; 5-(4-(((3s,5s,7s)-adamantan-1-yl)carbamoyl)-5-methyl-1-phenyl-1H-imidazol-2-yl)pentyl nitrate; 5-(4-((1-cyanocyclopropyl)carbamoyl)-5-methyl-1-phenyl-1H-imidazol-2-yl)pentyl nitrate; 5-(4-((1,1-dioxidotetrahydro-2H-thiopyran-4-yl)carbamoyl)-5-methyl-1-phenyl-1H-imidazol-2-yl)pentyl nitrate; 5-(4-((1,1-dioxidothiomorpholino)carbamoyl)-5-methyl-1-phenyl-1H-imidazol-2-yl)pentyl nitrate; 5-(4-(5-(2,4-dichlorophenyl)-2-((1,1-dioxidothiomorpholino)carbamoyl)oxazol-4-yl)phenyl)pent-4-yn-1-yl nitrate; 4-(4-(2-((1-cyanocyclopropyl)carbamoyl)-5-(2,4-dichlorophenyl)oxazol-4-yl)phenyl)but-3-yn-1-yl nitrate; 4-(4-(5-(2,4-dichlorophenyl)-2-(piperidin-1-ylcarbamoyl)oxazol-4-yl)phenyl)but-3-yn-1-yl nitrate; 4-(4-(5-(2,4-dichlorophenyl)-2-(morpholinocarbamoyl)oxazol-4-yl)phenyl)but-3-yn-1-yl nitrate; 1-(4-(4-bromophenyl)-5-(2,4-dichlorophenyl)oxazole-2-carboxamido)piperid in-4-yl nitrate; 2-(nitrooxy)ethyl 2-(4-(5-(2,4-dichlorophenyl)-2-(piperidin-1-ylcarbamoyl)oxazol-4-yl)phenyl)-2-methylpropanoate; 5-(4-(5-(2,4-dichlorophenyl)-2-((1,1-dioxidothiomorpholino)carbamoyl)thiazol-4-yl)phenyl)pent-4-yn-1-yl nitrate; 4-(4-(2-((1-cyanocyclopropyl)carbamoyl)-5-(2,4-dichlorophenyl)thiazol-4-yl)phenyl)but-3-yn-1-yl nitrate; 4-(4-(5-(2,4-dichlorophenyl)-2-(piperidin-1-ylcarbamoyl)thiazol-4-yl)phenyl)but-3-yn-1-yl nitrate; 4-(4-(5-(2,4-dichlorophenyl)-2-(morpholinocarbamoyl)thiazol-4-yl)phenyl)but-3-yn-1-yl nitrate; 1-(4-(4-bromophenyl)-5-(2,4-dichlorophenyl)thiazole-2-carboxamido)piperidin-4-yl nitrate; 2-(nitrooxy)ethyl 2-(4-(5-(2,4-dichlorophenyl)-2-(piperidin-1-ylcarbamoyl)thiazol-4-yl)phenyl)-2-methylpropanoate; 5-(4-(1-(2,4-dichlorophenyl)-3-((1,1-dioxidothiomorpholino)carbamoyl)-1H-1,2,4-triazol-5-yl)phenyl)pent-4-yn-1-yl nitrate; 4-(4-(3-((1-cyanocyclopropyl)carbamoyl)-1-(2,4-dichlorophenyl)-1H-1,2,4-triazol-5-yl)phenyl)but-3-yn-1-yl nitrate; 4-(4-(1-(2,4-dichlorophenyl)-3-(piperidin-1-ylcarbamoyl)-1H-1,2,4-triazol-5-yl)phenyl)but-3-yn-1-yl nitrate; 4-(4-(1-(2,4-dichlorophenyl)-3-(morpholinocarbamoyl)-1H-1,2,4-triazol-5-yl)phenyl)but-3-yn-1-yl nitrate; 4-(3-((2R,4R)-4-(((R)-2,3-dihydro-1H-inden-1-yl)amino)-5-oxo-1-(4-(trifluoromethyl)phenyl)pyrrolidin-2-yl)phenyl)but-3-yn-1-yl nitrate; 4-(3-((2R,4R)-4-(((S)-2,3-dihydro-1H-inden-1-yl)amino)-5-oxo-1-(4-(trifluoromethyl)phenyl)pyrrolidin-2-yl)phenyl)but-3-yn-1-yl nitrate; 4-(3-((2R,4R)-5-oxo-4-(((R)-1-phenylethyl)amino)-1-(4-(trifluoromethyl)phenyl)pyrrolidin-2-yl)phenyl)but-3-yn-1-yl nitrate; 4-(3-((2R,4R)-5-oxo-4-(((S)-1-phenylethyl)amino)-1-(4-(trifluoromethyl)phenyl)pyrrolidin-2-yl)phenyl)but-3-yn-1-yl nitrate; 4-(3-((2R,4R)-5-oxo-4-(((R)-1,2,3,4-tetrahydronaphthalen-1-yl)amino)-1-(4-(trifluoromethyl)phenyl)pyrrolidin-2-yl)

phenyl)but-3-yn-1-yl nitrate; 4-(3-((2R,4R)-5-oxo-4-(((S)-1,2,3,4-tetrahydronaphthalen-1-yl)amino)-1-(4-(trifluoromethyl)phenyl)pyrrolidin-2-yl)phenyl)but-3-yn-1-yl nitrate; 4-(4-((3R,5R)-2-oxo-5-(3-(trifluoromethoxy)phenyl)-3-((2-(6-(trifluoromethyl)pyridin-2-yl)propan-2-yl)amino)pyrrolidin-1-yl)phenyl)but-3-yn-1-yl nitrate; 4-(4-((3R,5R)-2-oxo-5-(3-(trifluoromethoxy)phenyl)-3-((2-(6-(trifluoromethyl)pyridin-2-yl)propan-2-yl)amino)pyrrolidin-1-yl)phenyl)but-3-yn-1-yl nitrate; 4-(3-((2R,4R)-5-oxo-4-((2-(6-(trifluoromethoxy)pyridin-3-yl)propan-2-yl)amino)-1-(4-(trifluoromethyl)phenyl)pyrrolidin-2-yl)phenyl)but-3-yn-1-yl nitrate; 4-(3-((2R,4R)-5-oxo-4-((2-(6-(trifluoromethoxy)pyridin-3-yl)propan-2-yl)amino)-1-(4-(trifluoromethyl)phenyl)pyrrolidin-2-yl)phenyl)but-3-yn-1-yl nitrate; 4-(3-((2R,4R)-5-oxo-1-(4-(trifluoromethyl)phenyl)-4-((2-(2-(trifluoromethyl)pyrimidin-4-yl)propan-2-yl)amino)pyrrolidin-2-yl)phenyl)but-3-yn-1-yl nitrate; 4-(3-((2R,4R)-5-oxo-1-(4-(trifluoromethyl)phenyl)-4-((2-(2-(trifluoromethyl)pyrimidin-4-yl)propan-2-yl)amino)pyrrolidin-2-yl)phenyl)but-3-yn-1-yl nitrate; 4-(4-(3-(2,4-dichlorophenyl)-1-methyl-5-(piperidin-1-ylcarbamoyl)-1H-pyrrol-2-yl)phenyl)but-3-yn-1-yl nitrate; 4-(4-(3-(2,4-dichlorophenyl)-1-methyl-5-(morpholinocarbamoyl)-1H-pyrrol-2-yl)phenyl)but-3-yn-1-yl nitrate; 4-(4-(3-(2,4-dichlorophenyl)-5-((1-dioxidothiomorpholino)carbamoyl)-1-methyl-1H-pyrrol-2-yl)phenyl)but-3-yn-1-yl nitrate; 4-(4-(5-((1-cyanocyclopropyl)carbamoyl)-3-(2,4-dichlorophenyl)-1-methyl-1H-pyrrol-2-yl)phenyl)but-3-yn-1-yl nitrate; (R,Z)-4-(4-(1-(N'-((4-chlorophenyl)sulfonyl)-N-methylcarbamimidoyl)-4-phenyl-4,5-dihydro-1H-pyrazol-3-yl)phenyl)but-3-yn-1-yl nitrate; (R,Z)-4-(4-(N-((3-(4-chlorophenyl)-4-phenyl-4,5-dihydro-1H-pyrazol-1-yl)(methylamino)methylene)sulfamoyl)phenyl)but-3-yn-1-yl nitrate; (R,Z)-2-(3-(4-chlorophenyl)-N'-((4-chlorophenyl)sulfonyl)-4-phenyl-4,5-dihydro-1H-pyrazole-1-carboximidamido)ethyl nitrate; 4-(4-(1-(2,4-dichlorophenyl)-3-(piperidin-1-ylcarbamoyl)-4,5-dihydro-1H-pyrazol-5-yl)phenyl)but-3-yn-1-yl nitrate; 4-(4-(1-(2,4-dichlorophenyl)-3-(morpholinocarbamoyl)-4,5-dihydro-1H-pyrazol-5-yl)phenyl)but-3-yn-1-yl nitrate; 4-(4-(1-(2,4-dichlorophenyl)-3-((1-dioxidothiomorpholino)carbamoyl)-4,5-dihydro-1H-pyrazol-5-yl)phenyl)but-3-yn-1-yl nitrate; 4-(4-(3-((1-cyanocyclopropyl)carbamoyl)-1-(2,4-dichlorophenyl)-4,5-dihydro-1H-pyrazol-5-yl)phenyl)but-3-yn-1-yl nitrate; 4-(4-(3-(4-chlorophenyl)-6-((4,4-difluorocyclohexyl)carbamothioyl)pyrazin-2-yl)phenyl)but-3-yn-1-yl nitrate; 4-(4-(8-(2-chlorophenyl)-6-(4-(ethylamino)piperidine-4-carboxamido)-9H-purin-9-yl)phenyl)but-3-yn-1-yl nitrate; 4-(4-(2-(2-chlorophenyl)-8-(2-(methylsulfonyl)acetamido)-5,6,7,8-tetrahydro-2H-oxepino[3,2-c]pyrazol-3-yl)phenyl)but-3-yn-1-yl nitrate; 4-(4-(2-(2-chlorophenyl)-7-(2,2-difluoropropyl)-8-oxo-5,6,7,8-tetrahydro-2H-pyrazolo[3,4-f][1,4]oxazepin-3-yl)phenyl)but-3-yn-1-yl nitrate; 2-(1H-indol-3-yl)-2-phenylethyl nitrate; (R)-2-(1H-indol-3-yl)-2-phenylethyl nitrate; (S)-2-(1H-indol-3-yl)-2-phenylethyl nitrate; (6Z,9Z,12Z,15Z)-20-((2-hydroxyethyl)amino)-20-oxoicosa-6,9,12,15-tetraen-1-yl nitrate; (5Z,8Z,11Z,14Z)-19-((1,3-dihydroxypropan-2-yl)oxy)nonadeca-5,8,11,14-tetraen-1-yl nitrate; (5Z,8Z,11 Z,14Z)-19-((1,3-dihydroxy-2-methylpropan-2-yl)oxy)nonadeca-5,8,11,14-tetraen-1-yl nitrate; (6Z,9Z,12Z,15Z)-20-(cyclopropylamino)-20-oxoicosa-6,9,12,15-tetraen-1-yl nitrate; (6Z,9Z,12Z,15Z)-20-oxo-20-(prop-2-yn-1-ylamino)icosa-6,9,12,15-tetraen-1-yl nitrate; 2-phenyl-2-(2-phenyl-1H-indol-3-yl)ethyl nitrate; (R)-2-phenyl-2-(2-phenyl-1H-indol-3-yl)ethyl nitrate; (S)-2-phenyl-2-(2-phenyl-1H-indol-3-yl)ethyl nitrate.

DETAILED DESCRIPTION OF THE INVENTION

The inventive compounds in any formula, embodiment or variation include any and all possible isomers and stereoisomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

As used herein and in the appended claims, the singular forms "a", "an", and "the" include plural referents unless the context clearly dictates otherwise. Thus, for example, reference to "a solvent" includes a plurality of such solvents. As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology.

The term "compound(s) of the technology" as used herein means any of compounds of formulae I-XVI, and may include all of their enantiomers, diastereomers, geometric isomers, racemates, tautomers, rotamers, and atropisomers, N-oxides, salts, solvates, and/or hydrates, metabolites and pharmaceutically acceptable salts thereof. The compounds of the present technology are prepared in different forms, such as pharmaceutically acceptable salts, hydrates, or solvates and the technology includes compositions and methods encompassing all variant forms of the compounds.

As used herein, $C_m$-$C_n$, such as $C_1$-$C_{12}$, $C_1$-$C_8$, or $C_1$-$C_6$ when used before a group refers to that group containing m to n carbon atoms.

Unless otherwise specifically defined, "alkyl" or "lower alkyl" refers to a linear, branched or cyclic or cycloalkyl group having from 1 to 30 carbon atoms, 1 to 12 carbon atoms, and advantageously 1 to 7 carbon atoms including, for example, methyl, ethyl, propyl, butyl, hexyl, octyl, isopropyl, isobutyl, tert-butyl, cyclopropyl, cyclohexyl, and cyclooctyl. The alkyl group can be saturated or unsaturated. The alkyl group or the lower alkyl group can be unsubstituted, singly substituted or, if possible, multiply substituted, with substituent groups in any possible position. Unless otherwise specifically limited, a cyclic or cycloalkyl group includes carbocyclic, monocyclic, bicyclic, tricyclic, tetracyclic, spirocyclic and polycyclic rings.

Unless otherwise specifically defined, a "carbocyclic" ring and all its isomers has a ring structure, chiral or achiral, saturated or unsaturated, substituted or unsubstituted, with about 0 to 5 heteroatoms, and having about 3 to about 20 ring members, for example, 1- or 2-cyanocyclopropyl, 2,2,3,3-tetramethylcyclopropyl, cyclohexadiene, cyclohexanol, cycloheptane, cyclohexane, tetrahydropyran, cyclohexanone, cyclohexene, cyclohexadiene, lactone, lactam, sultone, sultam, quinone, and terpenes. The carbocyclic group and all of its isomers can be unsubstituted, singly substituted or, if possible, multiply substituted, with substituent groups in any possible position. Carbocyclic groups related to terpenes include p-mentha-2,8-dien-1-ol, p-mentha-1,8-diene-3-ol (isopiperitenol), nopinone and related derivatives, menthane, limonene, phellandrene, terpinolene, terpinene, menthol, isomenthol, neomenthol, neoisomenthol, pulegol, isopulegol, piperitol, terpineol, menth-1-en-8-thiol, carveol, perillaaldehyde, perillyl alcohol, menthone, isomenthone, pulegone, isopulegone, phellandral, piperitone, dihydrocarvone, carvenone, carvone, cymene, carvacrol, thymol, cymen-8-ol and cuminaldehyde. The terpenes will encompass all related isomers. In certain embodiments, the carbocyclic group can be fused to another carbocyclic group, for example as in octahydro-1H-indene. For example, carobocyclic groups comprising of lactones include α-acetolactone, β-propiolactone, γ-butyrolactone, δ-valerolactone and ε-caprolactone. For example, carobocyclic groups comprising of lactones include pyrrolidinone. In some instances, a carbocyclic group can also be a cyclic or cycloalkyl group, a heteroalkyl or a heterocyclic group, or an alkyl group.

Unless otherwise specifically defined, an "alkaloid" is a natural product as defined in the publication Alkaloids—Secrets of Life, Alkaloid Chemistry, Biological Significance, Applications and Ecological Role by Tadeusz Aniszewski, 2007, Elsevier B. V., herein incorporated by reference in its entirety. Examples include morphine, codeine, and thebaine. The "alkaloid" can be unsubstituted, singly substituted or, if possible, multiply substituted, with substituent groups in any possible position. In some embodiments, an alkaloid can also be a heterocyclic group or a heteroaromatic group.

Unless otherwise specifically defined, a "terpene" is a natural product as defined within and in the publication Terpenes—Flavors, Fragrances, Pharmaca, Pheromones (Eberhard Breitmaier, 2006, Wiley-VCH, incorporated herein by reference in its entirety). Examples of terpenes include camphor, pinene and menthol. The "terpene" can be unsubstituted, singly substituted or, if possible, multiply substituted, with substituent groups in any possible position. In some embodiments, a terpene can also be an carbocyclic group or an alkyl group. Unless otherwise specifically defined, a "terpene derivative" is a natural product or a synthetic compound that is obtained by a chemical modification of another parent terpene. For example, (+)-nopinone can be derived from β-pinene and. Similarly cis- and trans-isopiperitenol can be derived from the (+)-limonene Unless otherwise specifically defined, a lactone is a cyclic ester having 4 to 8 ring members. The lactone can be unsubstituted, singly substituted or, if possible, multiply substituted, with substituent groups in any possible position. Unless otherwise specifically defined, a lactam is a cyclic amide having 4 to 8 ring members. The lactam can be unsubstituted, singly substituted or, if possible, multiply substituted, with substituent groups in any possible position. Unless otherwise specifically defined, a sultam is a cyclic sulfonamide having 4 to 8 ring members in which the S—N bond is part of the ring. The sultam can be unsubstituted, singly substituted or, if possible, multiply substituted, with substituent groups in any possible position.

Unless otherwise specifically defined, a "bicyclic" ring comprises two fused or bridged rings. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, 2,3-dihydro-1H-indene, bicyclo[3.1.0]hexane, 2,3-dihydro-1H-inden-2-yl)methanol, bicyclooctane 7,7-dimethylbicyclo[2.2.1]hept-2-ene, 7,7-dimethylbicyclo[2.2.1]hept-2-en-1-yl)methanol, 7,7-dimethylbicyclo[2.2.1]heptane, 2,6-dioxabicyclo[3.3.0]octane, 6,6-dimethylbicyclo[3.1.1]heptan-2-one, tetralin, decalin and related terpenes such as carane, trans-thujane, pinane, camphene, isocamphane, fenchane, careen, chaminic acid, sabinene, thujene, thujol, thujanone, α-pinene, β-pinene, car-4-ene-3-ol, verbenol, verbenone, myrtenol, myrtenal, pinocarveol, pinocarvone, camphor, isoborneol, borneol, norbornane, fenchone, β-fenchol, α-fenchol, camphene and fenchene. The terpenes will encompass all related isomers and derivatives.

Unless otherwise specifically defined, a "tricyclic" ring comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position. The individual rings may or may not be of the same type. Examples of tricyclic ring structures include fluorene and anthracene.

Unless otherwise specifically defined, a "spirocyclic" ring is a non-aromatic ring structure wherein two rings are fused at one carbon atom and each ring can have 3 to 6 ring members independently selected from carbon atoms and one or more heteroatoms, including oxygen, nitrogen, phosphorous and/or sulfur or a combination thereof and S can exist as S, SO or $SO_2$. Examples include azaspiro[3.3]heptane, azaspiro[3.5]nonane, spiro[3.3]heptane, azaspiro[5.5]undecane, azaspiro[3.4]octane, azaspiro[2.4]heptane, diazaspiro[4.5]decane, diazaspiro[3.5]nonane, diazaspiro[3.3]heptane, diazaspiro[4.4]nonane, diazaspiro[6.6]tridecane, thia-6-azaspiro[3.3]heptane, dioxo-thia-6-azaspiro[3.3]heptane, oxa-6-azaspiro[3.3]heptane.

Unless otherwise specifically defined, a "polycyclic" ring comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantane, oxa-adamantane, bicyclooctane, norbornane and bicyclononanes.

Unless otherwise specifically defined, a "heterocyclic" ring is a saturated or unsaturated ring structure having about 3 to about 8 ring members independently selected from carbon atoms and one or more heteroatoms, including oxygen, nitrogen, phosphorous and/or sulfur; for example, azetidine, methylazetidine, piperidine, morpholine, piperazine, (S) and (R)-1,2-dimethylpiperazine, 1-H-pyridine-2-one, dihydropyridine, tetrahydropyridine, pyridazin-3(2H)-one, piperidine-2,4-dione, pyrrolidine, thiomorpholine, 1,1-dioxothiomorpholine, 4,4-difluoropiperidine, tetrahydro-2H-thiopyran 1,1-dioxide, nucleosides and their derivatives or an alkaloid. The heterocyclic ring can be unsubstituted, singly substituted or, if possible, multiply substituted, with substituent groups in any possible position. In some embodiments, a "heterocyclic" ring can be fused to other rings and also be referred to as a "heterobicyclic" ring, a "heterotricyclic" ring or a "heteropolycyclic" ring.

Unless otherwise specifically defined, a "heterobicyclic" ring structure comprises 2 fused or bridged rings having ring members independently selected from carbon and one or more heteroatoms, including oxygen, nitrogen, phosphorous and/or sulfur. The heterobicyclic ring structure can be saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include octahydropyrrolo[3,4-c]pyrrole and diazabicyclo[3.3.1]nonane and isobenzofuran.

Unless otherwise specifically defined, a "heterotricyclic" ring structure comprises 3 fused, bridged, or both fused and bridged rings having ring members independently selected from carbon and one or more heteroatoms, including oxygen, nitrogen, phosphorous and/or sulfur. The heterotricyclic ring structure may be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline, phenazine, 2,4,10-trioxaadamantane and tetradecahydro-phenanthroline.

Unless otherwise specifically defined, a "heteropolycyclic" ring structure comprises more than 3 rings that may be fused, bridged or both fused and bridged and that have ring members independently selected from carbon and one or more heteroatoms, including oxygen, nitrogen, phosphorous and/or sulfur. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantane, oxa-adamantane, tropane, homotropane and 5-norbornene-2,3-dicarboximide.

Unless otherwise specifically defined, "alkenyl" refers to a, straight or branched hydrocarbon chain containing 2 to 12 carbons and containing at least one carbon-carbon double bond. Representative alkenyl groups include vinyl, allyl, ethenyl, 2-propenyl, 2-methyl-2-propenyl, 2-methylhex-2-enyl, 3-butenyl, 2-methylpent-2-enyl, 3-methylocta-2,6-dienyl, 4-pentenyl, 5-hexenyl, 2-heptenyl, 2-methyl-1-heptenyl, and 3-decenyl or a terpene. The "alkenyl" group can be unsubstituted, singly substituted or, if possible, multiply substituted, with substituent groups in any possible position. Unless otherwise specifically defined, an unsaturated alkyl group can also be an alkenyl group.

Unless otherwise specifically defined, "alkenylene" refers to a divalent group derived from a straight or branched hydrocarbon chain containing 2 to 4 carbon atoms and containing at least one carbon-carbon double bond. Representative alkenylene groups include, CH=CH— and —CH$_2$CH=CH—. The "alkenylene" group can be unsubstituted, singly substituted or, if possible, multiply substituted, with substituent groups in any possible position. Unless otherwise specifically defined, an unsaturated alkyl group can also be an alkenyl group.

Unless otherwise specifically defined, "alkynyl" refers to a straight or branched chain hydrocarbon group containing 2 to 10 carbon atoms and containing at least one carbon-carbon triple bond. Representative alkynyl groups include acetylenyl, 1-propynyl, 2-propynyl, 3-butynyl, 2-pentynyl, and 1-butynyl. The "alkynyl" group can be unsubstituted, singly substituted or, if possible, multiply substituted, with substituent groups in any possible position. Unless otherwise specifically defined, an unsaturated alkyl group can also be an alkynyl group.

Unless otherwise specifically defined, "alcohol" refers to the general formula alkyl-OH or carbocyclic-OH, cyclic alkyl-OH, glycol, polyol, and includes primary, secondary and tertiary variations. The alcohol can be protected with a protecting group selected from Peter G. M. Wuts, Theodora W. Greene, Greene's Protective Groups in Organic Synthesis, 4th Edition, 2006, Wiley; herein incorporated by reference in its entirety. Examples of protecting groups include methyl, benzyl and acetyl. The "alcohol" group can be unsubstituted, singly substituted or, if possible, multiply substituted, with substituent groups in any possible position. Unless otherwise specifically defined, a glycol is an alcohol containing compound with two hydroxyl groups. The glycol group can be unsubstituted, singly substituted or, if possible, multiply substituted, with substituent groups in any possible position. Examples of glycol include 1,2-ethanediol, 1,3-propanediol and 1,4-butanediol.

Unless otherwise specifically defined, a polyol is an alcohol containing compound more than two hydroxyl groups. The polyol group can be unsubstituted, singly substituted or, if possible, multiply substituted, with substituent groups in any possible position.

Unless otherwise specifically defined, "alkoxy" refers to the general formula —O-alkyl.

Unless otherwise specifically defined, "aryloxy" refers to the general formula —O-aryl-.

Unless otherwise specifically defined, "heteroaryloxy" refers to the general formula —O-heteroaryl-.

Unless otherwise specifically defined, "arylalkoxy" refers to the general formula —O— alkyl-aryl-.

Unless otherwise specifically defined, "heteroarylalkoxy" refers to the general formula —O-alkyl-heteroaryl-.

Unless otherwise specifically defined, "arylalkyl" refers to the general formula, -aryl-alkyl- wherein the "aryl" and "alkyl" groups can be unsubstituted, singly substituted or, if possible, multiply substituted, with substituent groups in any possible position. Examples of "arylalkyl" include benzyl, benzhydryl, 1-phenylethyl, 2-phenylethyl, 4-phenylbutyl, and benzhydryloxy groups.

Unless otherwise specifically defined, "heteroarylalkyl" refers to the general formula, -heteroaryl-alkyl- wherein the "heteroaryl" and "alkyl" groups can be unsubstituted, singly substituted or, if possible, multiply substituted, with substituent groups in any possible position. Examples of "heteroarylalkyl" include benzyl, benzhydryl, 1-phenylethyl, 2-phenylethyl, 3-phenylpropyl, 4-phenylbutyl, and benzhydryloxy groups.

Unless otherwise specifically defined, "amine" refers to a compound containing a basic nitrogen, and is substituted.

Unless otherwise specifically defined, "amide" refers to the general formula —C(O)—N— or —N—C(O)—, and can be singly substituted or, if possible, multiply substituted, with substituent groups on the carbon or the nitrogen atom.

Unless otherwise specifically defined, "ester" refers to the general formula —C(O)—O— or —O—C(O)—, and can be substituted with substituent groups on the carbon or the oxygen atom.

Unless otherwise specifically defined, "acyl" refers to the general formula —C(O)alkyl.

Unless otherwise specifically defined, "acyloxy" refers to the general formula —O-acyl-.

Unless otherwise specifically defined, "alkylmercapto" refers to the general formula —S-alkyl, SO-alkyl- and —SO$_2$-alkyl, for example thiomorpholine, 1,1-dioxothiomorpholine.

Unless otherwise specifically defined, "arylmercapto" refers to the general formula —S-aryl, SO-aryl- and —SO$_2$-aryl.

Unless otherwise specifically defined, "heteroarylmercapto" refers to the general formula —S-heteroaryl, SO-heteroaryl- and —SO$_2$-heteroaryl.

Unless otherwise specifically defined, "alkylamino" refers to the general formula —(NH)-alkyl, for example methylamine, ethylamine, ethylenediamine, 2-aminoethanol.

Unless otherwise specifically defined, "arylamino" refers to the general formula —(NH)-aryl, for example aniline.

Unless otherwise specifically defined, "heteroarylamino" refers to the general formula —(NH)-heteroaryl, for example aminopyridine.

Unless otherwise specifically defined, "di-alkylamino" refers to the general formula —N-(alkyl)$_2$. Unless otherwise specifically limited di-alkylamino includes cyclic amine compounds such as piperidine and morpholine and 1,1-dioxothiomorpholine.

Unless otherwise specifically defined, an "aromatic" ring is an unsaturated ring structure having about 6 to 12 ring members, for example benzene. In some instances, "aromatic" ring is an unsaturated ring structure that can be fused to another unsaturated ring structure, ex. naphthalene. The aromatic ring structure can be unsubstituted, singly substituted or, if possible, multiply substituted, with substituent groups in any possible position.

Unless otherwise specifically defined, "aryl" refers to an "aromatic" ring, for example phenyl, biphenyl, fluorenyl, dibenzosuberanyl, dibenzosuberenyl, or naphthyl. The aryl group can be unsubstituted, singly substituted or, if possible, multiply substituted, with substituent groups in any possible position. In certain embodiments, the aryl group will be fused to a carbocyclic ring having 4 to 8 ring atoms, for example as in 2,3-dihydro-1H-indene, 2,3-dihydro-1H-inden-2-yl)methanol and 2,2-dimethyl-2,3-dihydro-1H-indene. In certain embodiments, the aryl group will be fused to a heterocyclic ring having from 5 to 8 ring atoms, for example as in chromane and 2,3-dihydrobenzofuran.

Unless otherwise specifically defined, "aroyl" refers to the general formula —C(=O)aryl.

The "aroyl" group can be unsubstituted, singly substituted or, if possible, multiply substituted, with substituent groups in any possible position Unless otherwise specifically defined, "halogen" refers to an atom selected from fluorine, chlorine, bromine and iodine.

Unless otherwise specifically defined, a "heteroaromatic" ring is an unsaturated ring structure having about 5 to about 8 ring members independently selected from carbon atoms and one or more heteroatoms, including oxygen, nitrogen, phosphorous and/or sulfur, for example, thiophene, oxazole, isoxazole, imidazole, pyrazole, benzimidazole, triazolopyridine, benzotriazole, pyridine, pyridine 1-oxide, pyrimidine, indole, indazole, furan, quinoline, 1,2,4-triazole, 1,2,3-triazole, imidazole, tetrazole, methyltetrazole, 3,4-dihydro-1H-benzo[c][1,2]thiazine-2,2-dioxide, 1H-pyrrolo[2,3-c]pyridine, 1H-pyrrolo[2,3-b]pyridine, 1-(cyclohexylmethyl)-1H-benzo[d]imidazole, 1-((1-methylpiperidin-2-yl)methyl)-1H-indole, 2,3,4,9-tetrahydro-1H-carbazole, 1,2,3,4-tetrahydropyrrolo[3,4-b]indole, 4-(alkylsulfonyl)-1,2,3,4-tetrahydropyrrolo[3,4-b]indole, quinazolin-4(3H)-one, 4-((1H-indol-1-yl)methyl)tetrahydro-2H-thiopyran 1,1-dioxide, isoindolin-1-one, nucleosides and their derivatives or and alkaloid. The heteroaromatic ring can be unsubstituted, singly substituted or, if possible, multiply substituted, with substituent groups in any possible position. In certain embodiments, the heteroaryl group will be fused to a carbocyclic group having 5 to 8 ring atoms, for example as in 4,5,6,7-tetrahydrobenzo[b]thiophene, 4,4a,5,5a-tetrahydro-1H-cyclopropa[4,5]cyclopenta[1,2-c]pyrazole and 4,5,6,7-tetrahydro-1H-indole. In certain embodiments, the heteroaryl group will be fused to a heterocyclic ring having from 5 to 8 ring atoms, for example as in 5,6,7,8-tetrahydroquinoline. Unless otherwise specifically defined, a "heteroaromatic" ring is also referred to as "heteroaryl" ring. In some instances, an unsaturated "aryl" ring or unsaturated "aromatic" ring can be referred to as a "heteroaryl" ring or an "heteroaromatic" ring when the ring includes at least one heteroatom.

Unless otherwise specifically defined, the term "phenacyl" refers to the general formula phenylacyl.

In general, "substituted" or "optionally substituted" or "substituent" refers to a group or groups (e.g., an alkyl group, an aryl group) in which one or more bonds to an atom ex. hydrogen, contained therein may be replaced by a bond to non-hydrogen or non-carbon atoms. As used herein, and unless otherwise excluded, any alkyl, alkenyl, alkynyl, alkenylene, carbocyclyl, aryl, heteroaryl, cyclyl, or heterocyclyl may be substituted. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Substituent groups for the above moieties useful in the technology are those groups that do not significantly diminish the biological activity of the compound. Examples of substituent groups include, but are not limited to, alkyl, aryl, heteroaryl, alkynyl, alkenyl, alcohol, halogens (i.e., F, Cl, Br, and I); hydroxyls; alkoxy, alkenoxy, alkynoxy, aryloxy, arylalkoxy, heteroarylalkoxy, aryloxy or heteroaryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. In some embodiments, suitable substituents also include, terpene, boronic acid, boronate ester, BF$_3$K, biotin group tethered via an amide bond, CF$_2$, CF$_3$, CF$_2$H, N$_3$, NCS, CN, NQ$^1$Q$^1$, =O, OQ$^3$, SQ$^3$, NHQ$^3$, =CH$_2$, =NOH, OAc, O-acyl, O-aryl, CH$_2$-aryl, O-aroyl, NH-acyl, NH-aroyl, CHO, C(halogen)$_3$, (halogen)$_2$, COOQ$^3$, SO$_2$-halogen, OSO$_2$CF$_3$, SO$_3$H, SO$_3$alkyl, SO$_2$NQ$^1$Q$^1$, CONQ$^1$Q$^1$, =CH$_2$, OH, alkyl-OH, OH, ONO$_2$, alkyl-ONO$_2$, spirocyclic, alkylmercapto, aryl, aroyl, alkylamino, di-alkylamino, polycyclic, carbocyclic group, heterocyclic ring, aromatic ring, heteroaromatic ring, CO-T$^1$, —C(O)OP(O)(Oalkyl)$_2$, O—PO(OX$^1$)(OY$^1$), O-alkyl-(CH$_2$)$_p$—O—PO(OX$^1$)(OY$^1$) wherein p is 0-6, OSO$_3$H, OCO-alkyl-COOH, OCO-alkenyl-COOH, OPO$_3$H$_2$, O—SO$_2$alkyl-T$^1$, O—SO$_2$-T$^1$, OT$^1$, Oalkyl-T$^1$, NHSO$_2$-T$^1$, Nalkyl-SO$_2$-T$^1$, —O-COalkyl-T$^1$, NHCO-T$^1$, OCONH-T$^1$, O—CO-T$^1$, O—CO—O-T$^1$, OCO-alkyl-NH-T$^1$, OCO-alkyl-N(T$^1$)$_2$, OCO-alkyl-T$^1$, O-alkyl-T$^1$, O-alkyl-OCO-T$^1$, O-T$^1$-T$^1$, O-alkyl-PO(OX$^1$)(OY$^1$), OCO(glycol), OCO-alkyl(glycol), OCO-PEG$_r$, O—CO—O-PEG$_r$, O—COCO—O-PEG$_r$, and O-PEG$_r$ or a group comprising ONO$_2$; wherein T$^1$ is H, alkyl, halogen, OH, CF$_3$, CF$_2$H, COOH, COOalkyl, alkaloid, immunogen, terpene, O—PO(OX$^1$)(OY$^1$), SO$_3$H, ONO$_2$ a heterocyclic ring, NQ$^1$Q$^1$, or T$^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents;

r is 0 to 10;

wherein any of the above groups can be optionally substituted in any possible position;

$Q^1$ and $Q^1$ are each independently H, alkyl, or alkyl-$ONO_2$, or $Q^1$ and $Q^1$ together are part of a heterocyclic ring having about 4 to about 7 ring members and optionally one additional heteroatom selected from O, N or S, or $Q^1$ and $Q^1$ together are part of an imide ring having about 5 to about 6 members;

$Q^3$ is H, alkyl, heterocyclic ring, aromatic ring, heteroaromatic ring hydroxyloweralkyl, or alkyl-$NQ^1Q^1$;

$X^1$ and $Y^1$ are independently H, alkyl-OCO-alkyl, alkyl-O—CO—O-alkyl, alkali metals or alkaline earth metals; and $PEG_r$ refers to a polyether PEGylated group tethered via a linker. Unless otherwise specifically defined, "PEG", "$PEG_n$", "$PEG_r$", and "$PEG_s$" independently refer to the polyether entity tethered or conjugated to the compounds directly, via an alkyl group or via another linker to improve the physicochemical properties such as water solubility of the compounds. "PEG", "$PEG_n$", "$PEG_r$", and "$PEG_s$" can be represented by the formula —$(CH_2—CH_2—O—)_m$—$CH_3$ where m is 1-15. Examples of a linker are the amide group, carbamate, carbonate and the ester group. The linker can be hydrolyzed physiologically or enzymatically. The definitions and immediate applications of the PEG technology can be adapted from Valentino J. Stella (editor), Prodrugs: Challenges and Rewards, 2007, Springer (volumes 1 and 2); herein incorporated by reference in its entirety.

Unless otherwise specifically defined, the term "cannabinergic" refers to being related to or acting on the endocannabinoid system comprising of CB1 and CB2 receptors and additionally the orphan receptors GPR18, GPR55, and GPR119.

Unless otherwise specifically defined, the term "related analogs" refers to compounds disclosed in the technology that have the same properties as cannabinergic compounds. For example, the related analogs can bind covalently to the cannabinoid receptors and/or can act as nitric oxide donors or behave as cannabinergic agonists, antagonists, partial agonists or allosteric modulators.

Unless otherwise specifically defined, the term "dual functional behavior" refers to compounds disclosed in the technology that have more than one kind of an effect as shown in a standard in vitro assay. For example, a compound of the present technology can behave as a CB1 antagonist as well as a CB2 agonist. The standard in vitro assay can be one or more selected from the cAMP accumulation assay, GTP-γS binding assay, cell impedance assay, calcium mobilization assay or the β-arrestin recruitment assay. In some instances, a compound disclosed in the invention can behave as an orthosteric ligand, allosteric ligand or a biotopic ligand for the cannabinoid receptors. Unless otherwise specifically defined, an orthosteric ligand binds to an orthosteric site which refers to the endogenous agonist-binding site on a receptor. Unless otherwise specifically defined, an allosteric ligand binds to an allosteric site which refers to a binding site on the receptor that is topographically distinct from the endogenous agonist-binding (orthosteric) site. Bitopic ligands that have both orthosteric ligand-binding properties as well as a secondary element that is able to bind to a neighbouring allosteric site on the receptor. (Annu Rev Pharmacol Toxicol. 2012; 52:153-78, Nat Rev Drug Discov. 2013; 12(1):25-34, Annu Rev Pharmacol Toxicol. 2013; 53:531-56; herein incorporated by reference in its entirety).

Unless otherwise specifically defined, the term "bind covalently to cannabinoid receptors" and "label the cannabinoid receptors" refers to the cannabinoid receptors being temporarily or permanently modified. The modification happens when a chemical species belonging to the compounds attaches itself to the amino acid residues such as serines and cysteines of the cannabinoid receptors via a covalent bond.

Unless otherwise specifically defined, the term "agonist" refers to a compound which decreases the cAMP levels; an "antagonist" or "neutral antagonist" has no effect on cAMP levels; a "partial agonist" induces sub-maximal decrease in cAMP levels; and an "inverse agonist" increases the cAMP levels.

Unless otherwise specifically defined, the term "physicochemical properties" refers to certain physical and chemical descriptive properties that the compounds possess. For example, compound 1 has a better ClogP (octanol-water partition coefficient) and tPSA (total polar surface area) value of 4.2 and 90.5 respectively as compared to $\Delta^9$-THC which has a ClogP and tPSA of 7.2 and 29.4.

In various embodiments, the compounds disclosed herein may suitably include isomers, pharmaceutically acceptable salts, solvates, hydrates, amides, esters, ethers, chemically protected forms, tautomers, polymorphs and prodrugs thereof.

The term "composition(s) of the technology" as used herein means compositions comprising any of compounds described herein, such as for example, compounds of formulae (I)-(IX), or salts, tautomeric forms, hydrates, and solvates thereof.

The term "method(s) of the technology" as used herein means methods comprising treatment with the compounds and/or compositions of the technology.

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds described herein, or pharmaceutically acceptable salts, tautomers, solvates, or hydrates thereof, with other chemical components, such as physiologically acceptable carriers and excipients. The purpose of a pharmaceutical composition is to facilitate administration of a compound to an organism.

The term "pharmaceutically acceptable" refers to safe and non-toxic for in vivo, preferably, human administration.

The term "pharmaceutically acceptable salt" is intended to include salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoracetic, trichloroacetic, naphthalene-2 sulfonic, oxalic, propionic, and other acids. Salts may also exist as solvates or hydrates. Other exemplary pharmaceutically acceptable salts are described herein.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of (+) or (−) 20 percent, 10 percent, 5 percent or 1 percent.

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction, or one or more symptoms thereof, prevent the advancement of conditions related to an affliction, prevent the recurrence, development, or onset of one or more symptoms associated with an affliction, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin (herein incorporated by reference in its entirety).

As used herein, the terms "animal," "subject" and "patient" as used herein include all members of the animal kingdom including, but not limited to, mammals, animals (e.g., cats, dogs, horses, swine, etc.) and humans. In some embodiments, an "individual" refers to a human. In some embodiments, an "animal" refers to, for example, nonhuman-primates such as monkeys and baboons; veterinary animals, such as rodents, dogs, cats, horses and the like; and farm animals, such as cows, pigs and the like. In some embodiments, the subject or patient is a human.

The term "group comprising $ONO_2$" as used herein includes any moiety having a terminal —$ONO_2$ group. Such moieties include, but are not limited to, $ONO_2$, alkyl-$ONO_2$, O-alkyl-$ONO_2$, O—$SO_2$-alkyl-$ONO_2$, —C(O)O-alkyl-$ONO_2$, alkyl-C(O)O-alkyl-$ONO_2$, alkyl-O-alkyl-$ONO_2$, and the like. In some embodiments, the alkyl group is substituted with one or more groups selected from hydroxyl, carboxyl, carboalkoxy, amide, amino, cycloalkyl, aryl, heteroaryl, or heterocyclyl groups.

Unless otherwise specifically defined, in some instances $ONO_2$ refers to the term "nitric oxide donor". The "nitric oxide donor" in some instances can donate nitric oxide (NO). In some instances, the term "nitric oxide donor" is used to designate a chemical entity with the potential to elicit a NO(-like) response in living systems. Such compounds need not, in a literal sense, donate (or even spontaneously evolve) bioactive NO under physiological conditions.

Some of the inventive compounds show a high affinity for at least one of the cannabinoid receptors. Thus, another aspect of the invention is use of at least one of the inventive compounds to interact with a cannabinoid receptor.

Some of the novel cannabinergic derivatives disclosed in the invention show selectivity for the CB1 or the CB2 cannabinoid receptor. These inventive CB1 or CB2 selective analogs are able to interact with one of the CB1 or CB2 cannabinoid receptors present in the CNS as well as the periphery without affecting the other receptors to the same degree. Therefore, still another aspect of the invention is use of at least one of the inventive compounds to interact with both CB1 and CB2 cannabinoid receptors present either in the CNS or the periphery.

The inventive cannabinergic derivatives disclosed in the invention described herein, and physiologically acceptable salts thereof, have pharmacological properties when administered in therapeutically effective amounts for providing a physiological response. Thus, another aspect of the invention is the administration of a therapeutically effective amount of at least one of the inventive compounds, or a physiologically acceptable salt thereof, to an individual or animal to provide a physiological response.

A better understanding of the invention will be obtained from the following detailed description of the article and the desired features, properties, characteristics, and the relation of the elements as well as the process steps, one with respect to each of the others, as set forth and exemplified in the description and illustrative embodiments.

As used herein a "therapeutically effective amount" of a compound, is the quantity of a compound which, when administered to an individual or animal, results in a sufficiently high level of that compound in the individual or animal to cause a physiological response, for example a discernible increase or decrease in stimulation of cannabinoid receptors. The inventive compounds described herein, and physiologically acceptable salts thereof, have pharmacological properties when administered in therapeutically effective amounts individually or in combination for providing a physiological response useful to treat marijuana abuse, obesity, lifestyle choices such as a desire to lose weight, other metabolic disorders including improvement in lipid profiles and insulin related deficiencies, weight loss in patients with type 2 diabetes mellitus, weight loss in patients with Prader Willi Syndrome, diabetic nephropathy, hepatic disease such as hepatitis C virus, Non-alcoholic fatty liver disease, alcoholic fatty liver disease, non-alcoholic steatohepatitis, cardiometabolic diseases, congestive obstructive pulmonary disorders, inflammatory bowel disease, smoking cessation, bone defects, arthritis, inflammation, benign prostatic hypertrophy, radiation-induced pulmonary fibrosis, asthma, migraine, chronic-intestinal pseudo obstruction, constipation, schizophrenia, epilepsy, stress, memory disorders, migraine, vomiting, thymic disorders, dyskinesia, kinetic disorder, anxiety disorders, psychotic disorders, cognitive disorders, appetite disorders, mood disorders, delirious disorders, neuropathies, Parkinson's disease, Alzheimers disease, depression, psychosomatic-induced disease, diabetes, sexual dysfunctions, as well as for alcohol, opioid, nicotine and cocaine addiction, etc. Additionally, these analogs can be useful in cancer chemotherapy. Typically, a "therapeutically effective amount" of an inventive compound is believed to range from about 0.01 mg/day to about 1,000 mg/day.

As used herein, an "individual" refers to a human. An "animal" refers to, for example nonhuman-primates such as monkeys and baboons, veterinary animals, such as rodents, dogs, cats, horses and the like, and farm animals, such as cows, pigs and the like In a certain embodiments, the compound disclosed in the invention can be used in combination with other acceptable pharmaceutical substances.

In embodiments in which compounds of the disclosure is used in combination with other compounds, it will be possible to reduce or even eliminate one or more side-effects. A particular method involves administering a therapeutically effective amount of at least one of the compounds of the disclosure in combination with other compounds disclosed so as to reduce the side-effects in that individual.

As will be apparent, the compounds of the invention can be used alone or in combination with other CB1 receptor antagonists or anti-obesity agents known to the field. Examples of such agents include SR141716A (Acomplia®/ Rimonabant, 5-(4-chlorophenyl)-1-(2,4-dichlorophenyl)-4-methyl-N-(piperidin-1-yl)-1H-pyrazole-3-carboxamide), Xenical® (Orlistat, (S)—(S)-1-((2S,3S)-3-hexyl-4-oxooxetan-2-yl)tridecan-2-yl 2-formamido-4-methylpentanoate), Meridia® (Sibutramine, 1-(1-(4-chlorophenyl)cyclobutyl)-N,N,3-trimethylbutan-1-amine, hydrochloride monohydrate), SR147778 (Surinabant, 5-(4-bromophenyl)-1-(2,4-dichlorophenyl)-4-ethyl-N-(piperidin-1-yl)-1H-pyrazole-3-carboxamide), AVE-1625 (Drinabant, N-[1-[bis(4-chlorophenyl)methyl]-3-azetidinyl]-N-(3,5-difluorophenyl)-methanesulfonamide), CP-945,598 (Otenabant, 1-[8-(2-Chlorophenyl)-9-(4-chlorophenyl)-9H-purin-6-yl]-4-(ethylamino)piperidine-4-carboxamide), E-6776 (Rosonabant, 5-(4-chlorophenyl)-1-(2,4-dichlorophenyl)-N-(piperidin-1-yl)-4,5-dihydro-1H-pyrazole-3-carboxamide), MK-0364 (Taranabant, N-((2S,3S)-4-(4-chlorophenyl)-3-(3-cyanophenyl)butan-2-yl)-2-methyl-2-((5-(trifluoromethyl)pyridin-2-yl)oxy)propanamide), SLV-319 (Ibipinabant, (S,E)-3-(4-chlorophenyl)-N'-((4-chlorophenyl)sulfonyl)-N-methyl-4-phenyl-4,5-dihydro-1H-pyrazole-1-carboximidamide), V24343, Qsymia (Qnexa, Phentermine/topiramate, 2-methyl-1-phenylpropan-2-amine and 2,3:4,5-Bis-O-(1-methylethylidene)-β-D-fructopyranose sulfamate), Contrave (Bupropion/naltrexone, 2-(tert-butylamino)-1-(3-chlorophenyl)propan-1-one and 17-(cyclopropylmethyl)-4,5α-epoxy-3,14-dihydroxymorphinan-6-one), Empatic (Bupropion/zonisamide, 2-(tert-butylamino)-1-(3-chlorophenyl)propan-1-one and benzo[d]isoxazol-3-ylmethanesulfonamide), lorcaserin (Belviq, (1R)-8-chloro-1-methyl-2,3,4,5-tetrahydro-1H-3-benzazepine), and Phentermine (2-methyl-1-phenylpropan-2-amine).

Compounds of the invention can also be used in combination with a potassium channel opener, opiod antagonist, anticonvulsant agent, contraceptive agent, antipsychotic agent, 5-HT2C receptor agonist, anticonstipation agent, nicotine receptor agonist or partial agonist, CB2 agonist, melanin-concentrating hormone receptor antagonist, antipsychotic agents, peroxisome proliferator-activated receptors agonists, ghrelin antagonists, GLP-1 agonist, fatty acid amide hydrolase inhibitor, an intestinal-acting microsomal triglyceride transfer protein inhibitor, a dipeptidyl-peptidase IV inhibitor, a statin, a sterol absorption inhibitor (β-lactam), Beta-3 adrenergic agonist, a biguanide, Sodium glucose transport (SGLT2) antagonist, cyclooxygenase-2 inhibitor, renin inhibitor, monoamine oxidase inhibitor, CETP inhibitor, acetylcholinesterase inhibitor, ACAT inhibitor, DGAT-1 inhibitor, Mitochondrial Transfer Protein inhibitor, noradrenalin-serotonin-dopamine reuptake inhibitor or a lipase inhibitor. In some embodiments, this combination comprising the two pharmaceutically active ingredients can be in ratios ranging from 1:99 to 99:1. In some embodiments, this combination can comprise three pharmaceutically active ingredients in safe acceptable ratios that can cause a physiological response.

In one embodiment, less than five compounds of the disclosure, preferably one or two of same is used in combination with less than five of the known CB1 antagonists, preferably one or two of same.

In some embodiments, the compounds disclosed herein act covalently on the receptors.

In some embodiments, the compound exhibit fluorescent properties. The fluorescent compounds are typically endogenously fluorescent and do not rely on linking the cannabinoid compound to a fluorescent moiety In some embodiments, compounds disclosed herein are capable of labeling the amino acid residues within the cannabinoid receptor. Examples of the amino acid residues include, but are not limited to, cystines, serines, and tyrosines In some embodiments, compounds disclosed herein produce long lasting duration of action as they form a covalent bond to the cannabinoid receptors.

In some embodiments, any of the compounds disclosed herein could in itself act as a drug with a combination effect. For example compounds disclosed in the technology could dually act as a CB2 agonist as well as CB1 antagonist.

In one aspect, the compounds disclosed in the invention and related analogs have a range of useful medical applications by acting as agonists, partial agonists, neutral antagonists, inverse-agonists or allosteric modulators for the CB1, CB2 receptors and/or the orphan cannabinoid receptor. In some embodiments, the compounds exhibit dual functional behavior. In another aspect combination therapy, pharmaceutical preparations, and compositions employing the analogs are provided. In yet another aspect, methods of administering therapeutically effective amounts of the analogs to provide a physiological effect are provided.

For example compounds disclosed in the invention could dually act as a CB1 antagonist as well as 11β-hydroxy steroid dehydrogenase-1 inhibitor. In certain embodiments, the compound could act dually as a cannabinergic ligand as well as a nitric oxide donor.

By "physiologically acceptable salts" is meant, salts typically useful for pharmaceutical applications including acid addition salts and basic salts. Examples of acid addition salts are hydrochloride salts, hydrobromide salts, methane sulfonate salts etc. Examples of basic salts are salts where the cation is selected from alkali metals, such as sodium and potassium, alkaline earth metals, such as calcium, and ammonium ions. Other examples of physiologically acceptable salts can be found in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

Polymorphic forms show improved physiochemical properties and stability for formulation purposes. In one embodiment, the compounds disclosed in the invention could exist in various solid forms. The solid forms can be crystalline and amorphous forms, but not limited to, solvates, hydrates, hydrolyzable esters and N-oxides of the compounds defined in the specification. These solid forms can be obtained by treating either the free base or their salts at a certain adjusted pH and certain temperature with an solvent or a combination of solvents. The solvents can be and not limited to a hydrocarbon solvent such as toluene, xylene, hexanes, heptane, or petroleum ether, alcohol such as methanol, ethanol, n-butanol, n-propanol and 2-propanol, di-isopropyl ether, ethyl-acetate, dichloromethane, acetic acid, acetone, tetrahydrofuran, dichloromethane, and water.

In one embodiment, in order to improve or modify the bioavailability, onset and off-set of the compound disclosed in the present invention for the required physiological effect, a "pro-drug" of the same can be made available. For example, the pro-drug such as an in-vivo hydrolyzable ester can be a obtained by conjugation of the parent drug with a low-molecular weight alcohol or a high molecular weight polyethylene glycol(PEG). In certain embodiments, the compound disclosed in the invention could contain a nitrate ester group.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

In another embodiment, the compounds of the present disclosure can also comprise isotopes at one or more of their atoms. For example, the compounds can be radiolabeled with isotopes, such as $^2$H (deuterium written as D)$^3$H (tritium written as T), $^{11}$C (carbon-11), $^{13}$C (carbon-13), $^{14}$C (carbon-14), $^{15}$O (oxygen-15), $^{17}$O (oxygen-17), $^{18}$O (oxygen-18), $^{13}$N (nitrogen-13), $^{15}$N (nitrogen-15), $^{18}$F (fluorine-18), $^{75}$Br (bromine-75), $^{76}$Br (bromine-76), $^{77}$Br (bromine-77), $^{82}$Br (bromine-82), 123I (iodine-123), $^{124}$I (iodine-124), $^{125}$I (iodine-125) or $^{131}$I (iodine-131), $^{36}$Cl (chlorine-36) or $^{35}$S (sulphur-35), The present disclosure encompasses all isotopic variations of the described compounds, whether natural or unnatural, radioactive or not.

An isotope is one of two or more species of the same element. Each isotope of an element will have the same number of protons in its nucleus, the same atomic number and the same position in the Periodic Table. However each isotope of that element will have a different number of neutrons in its nucleus and therefore a different mass than other isotopes of that species. The term nuclide is sometimes used synonymously with the term isotope. As used herein a natural isotope has an atomic mass corresponding most closely with the atomic mass shown for that element in the Periodic Table. As used herein an unnatural isotope has an atomic mass that is different from the atomic mass shown for that element in the Periodic Table than the natural isotope. For example, protium (hydrogen-1 or $^1$H) is the natural isotope of hydrogen and deuterium (hydrogen-2 or $^2$H) and tritium (hydrogen-3 or $^3$H) are all unnatural isotopes of hydrogen.

In a particular embodiment, some of the halogen containing analogs, for example those analogs comprising iodide and fluoride, are potential radioactive probes for imaging in vivo the distribution of cannabinoid receptors. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

Some of the radioactive isotope containing analogs have potential as radiopharmaceutical analogs (disclosed analogs that have been labeled with radioactive isotopes). These radiopharmaceuticals can be administered to individuals or animals and the emitted radiation can be measured. The majority of these diagnostic tests involve the formation of an image using a camera suitable to detect the emitted radiation. Positron emission tomography (PET) is one nuclear medicine tomographic imaging technique, which produces a three-dimensional image or map of functional processes in a patient's body. To conduct the PET scan, a short-lived radiopharmaceutical analog that decays by emitting a positron is administered into the subject (usually by injection into the blood stream). There is a waiting period while the radiopharmaceutical analog becomes concentrated in tissues of interest such as a cannabinoid receptor. After the waiting period the patient is placed in an imaging scanner. The scanner collects multiple images and a computer is used to apply an algorithm to the multiple images and provide a three dimensional image. Single photon emission computed tomography (SPECT) is another nuclear medicine tomographic imaging technique. To conduct the SPECT scan, a short-lived radiopharmaceutical analog that decays to produce a gamma ray is administered into the subject. There is a waiting period while the radiopharmaceutical analog becomes concentrated in tissues of interest such as a cannabinoid receptor. After the waiting period the patient is placed in an imaging scanner and SPECT imaging is performed by using a gamma camera to acquire multiple two dimensional images from multiple angles. A computer is then used to apply an algorithm to the multiple images to provide a three dimensional image.

The invention will be further described in more detail by the following synthetic examples. These examples are offered to illustrate the invention, and are not to be construed in any way as limiting the scope of the invention.

EXAMPLES

Example 1

4-(4-(1-(2,4-dichlorophenyl)-4-methyl-3-(piperidin-1-ylcarbamoyl)-1H-pyrazol-5-yl)phenyl)but-3-ynyl nitrate (Compound 1)

To a stirred solution of compound 5 [1-(2,4-dichlorophenyl)-5-(4-(4-iodobut-1-ynyl)phenyl)-4-methyl-N-(piperidin-1-yl)-1H-pyrazole-3-carboxamide](60 mg, 0.9 mmol) taken in acetonitrile (20 ml) and to that silver nitrate (33.5 mg, 0.19 mmol) was added. The reaction mixture was heated for 2 hours. After cooling to RT, the precipitate was filtered. The filtrate was concentrated to give an oily residue which was subsequently dissolved in dichloromethane (20 ml). This was washed with 2×5 ml water and the organic layer was dried over anhydrous sodium sulfate, filtered, and evaporated. Flash column chromatography on silica gel with petroleum ether/ethyl acetate (1:1) gave compound 2 (40 mg, 74.6% yield) as a white solid.

$^1$H NMR (500 MHz, CDCl$_3$-d) 7.65 (s, 1H), 7.43 (s, 1H), 7.36 (d, J=8.30 Hz, 2H), 7.29-7.33 (m, 2H), 7.07 (d, J=8.30 Hz, 2H), 4.64 (t, J=6.84 Hz, 2H), 2.74-3.02 (m, 6H), 2.39 (s, 3H), 1.69-1.90 (m, 4H), 1.45 (br. s., 2H); m/z 542 (M+H)

Example 2

5-(3-(((3s,5s,7s)-adamantan-1-yl)carbamoyl)-4-methyl-5-phenyl-1H-pyrazol-1-yl)pentyl nitrate (Compound 2)

$^1$H NMR (500 MHz, CDCl$_3$-d) δ 7.40-7.52 (m, 3H), 7.24 (s, 2H), 6.72 (s, 1H), 4.36 (t, J=6.59 Hz, 2H), 3.99 (t, J=7.08 Hz, 2H), 2.21 (s, 3H), 2.15-2.19 (m, 6H), 2.09-2.15 (m, 3H), 1.67-1.79 (m, 8H), 1.61 (quin, J=1.00 Hz, 2H), 1.26 (quin, J=7.69 Hz, 2H); m/z 467 (M+H)

Example 3: Membrane Preparations from Tissue Culture Sources

HEK293 cells expressing hCB1, hCB2 or mCB2 receptor are used for membrane preparations according to the method described in *J Neurochem* 1999, 72, (5), 2032-8, herein incorporated by reference in its entirety. The resulting pellet is resuspended in 10 mM Tris-chloride, pH 7.4 with 5 mM MgCl$_2$ and 2 mM EDTA (TME), and stored at −80° C. for no longer than two months. Protein content is assayed by using the Bio-Rad DC protein assay according to the manufacturer's protocol.

Example 4: Membrane Preparations from Tissue Sources

Frozen rat brains (CB1 source) are obtained from Pel-Freeze Biologicals (Rogers, Ak.) and stored at −80° C. until use. Membranes are prepared according to the method described in *Brain Res* 1981, 226, (1-2), 107-18 and adapted as previously reported in *J Med Chem* 1994, 37, (23), 3867-70 and *Life Sci* 1995, 56, (23-24), 1957-62; each herein incorporated by reference in its entirety.

Example 5: rCB1, hCB2, and mCB2 Binding Assays

The compounds are tested for their ability to bind to CB1 and CB2 receptors using rat brain or HEK293 cell membranes expressing hCB2 and mCB2 membrane preparations, respectively, as described in *J Med Chem* 1999, 42, (4), 769-776, *J Med Chem* 1994, 37, (23), 3867-70 and *Life Sci* 1995, 56, (23-24), 1957-62 (each herein incorporated by reference in its entirety) via competition-equilibrium binding using [$^3$H]CP-55,940. The results are analyzed using nonlinear regression to determine the actual IC$_{50}$ of the ligand (Prizm by GraphPad Software, Inc.) and the Ki values are calculated from the IC$_{50}$ as described in *Biochemical Pharmacology* 1973, 22, (23), 3099-3108; herein incorporated by reference in its entirety. The CB1 cannabinoid receptor binding affinities (Ki) for some of the compounds disclosed in the invention range between 0.1 nM and less than 100 nM. The CB2 cannabinoid receptor binding affinities (Ki) for the synthesized analogs range between 0.1 nM and greater than 5000 nM. For example, CB1 cannabinoid receptor binding affinity (Ki) for compound 1 is less than 10 nM and the CB2 cannabinoid receptor binding affinity (Ki) is greater than 10 nM; the CB1 cannabinoid receptor binding affinity (Ki) for compound 2 is less than 10 nM and the CB2 cannabinoid receptor binding affinity (Ki) is less than 10 nM. The CB1 selectivity for some of the compounds range from 1 to greater than 5000. The CB2 selectivity for some of the compounds range from 1 to greater than 5000.

Example 6: Covalent Binding Assessment Assay and Electrophilic Labeling

Figure 2:
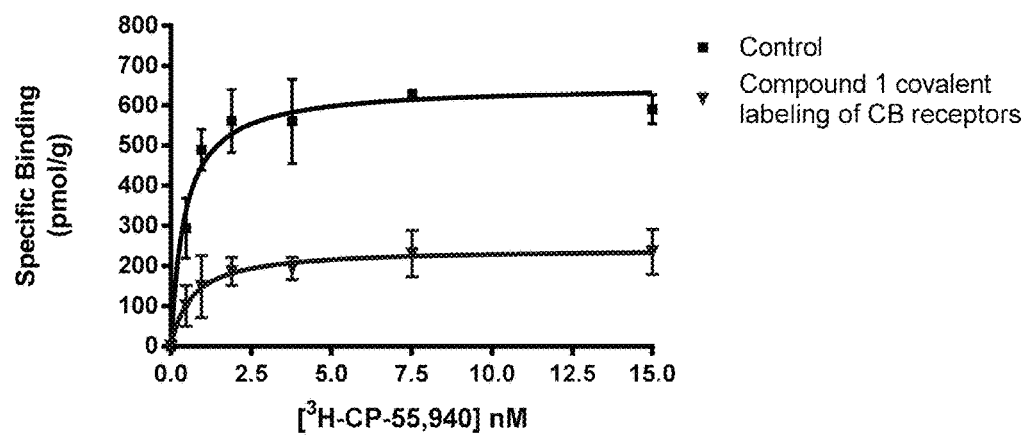
FIG. 2 illustrates covalent binding of Compound 1 to the CB1 Cannabinoid receptor.
Figure 3:
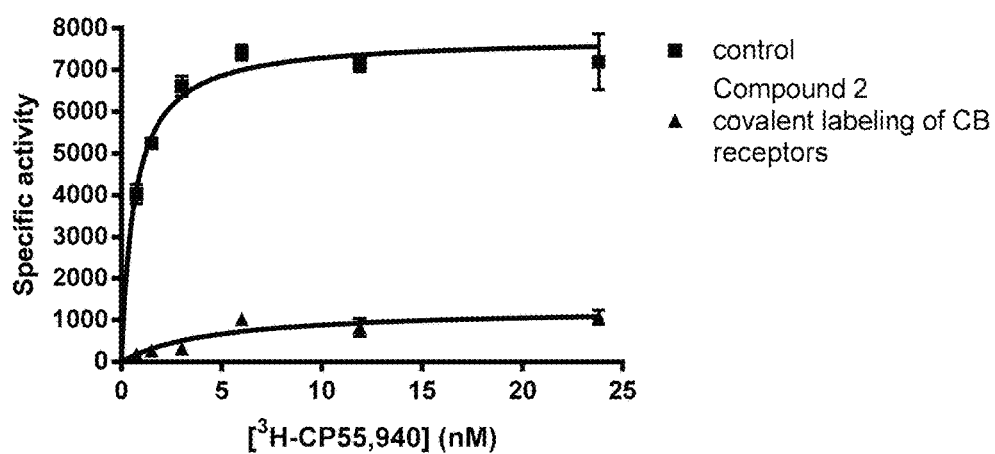
FIG. 3 illustrates covalent binding of Compound 2 to the CB2 Cannabinoid receptor.

The electrophilic covalent ligand possessing sufficiently high affinities for the receptors in the competition binding assays are evaluated for their abilities to irreversibly occupy CB1 and/or CB2 receptor sites using similar methods described in *J Proteome Res.* 2011, 10(10):4789-98, *Chem Biol.* 2010, 17(10):1132-42, *Chem Biol.* 2008, 5(11):1207-19, *Mol Pharm*, 2005, 68(6), 1623-1635, *J Med Chem.* 2005, 48(20):6423-9, *J. Org. Chem.* 2003, 68 (1), 55-61, *J Neurochem.* 2000, 74(5):2174-81, *Life Sci.* 1995, 56(23-24): 1957-62, *J. Med. Chem.* 1994, 37 (23), 3867-3870, *J. Med. Chem.* 1992, 35 (16), 3076-3079; each herein incorporated by reference in its entirety. For example, the covalent binding for Compound 2 to CB2 is shown in FIG. 2 and the covalent binding for Compound 1 to CB1 is shown in FIG. 1.

Example 7: Functional Assays

Ligands are evaluated for their abilities to behave as agonists, partial-agonists, neutral antagonists, or inverse agonists at CB1 and CB2 sites. HEK293 cells transfected with rCB1, mCB2, or hCB2 receptor are used with the PerkinElmer's Lance ultra cAMP kit following the protocol as described in *J Biomol Screen* 1999, 4, (6), 303-308; herein incorporated by reference in its entirety. The assays are carried out in 384-well format using 1000 cells/well. Test compounds are added to wells containing stimulation buffer and 2 μM forskolin followed by cell suspension. After 30 minutes stimulation, the Eu-cAMP tracer and Ulight-anti-cAMP are added to the plate and incubated at room temperature for 1 h prior to detection via PerkinElmer Envision; data are analyzed using GraphPad Prism software. For example compound 2 did not change the forskolin-stimulated cAMP accumulation in CB1 transfected HEK cells while it behaved as a CB2 antagonist (EC$_{50}$ less than 20 nM).

Example 8: Antinociception in Male Mice

Figure 4:
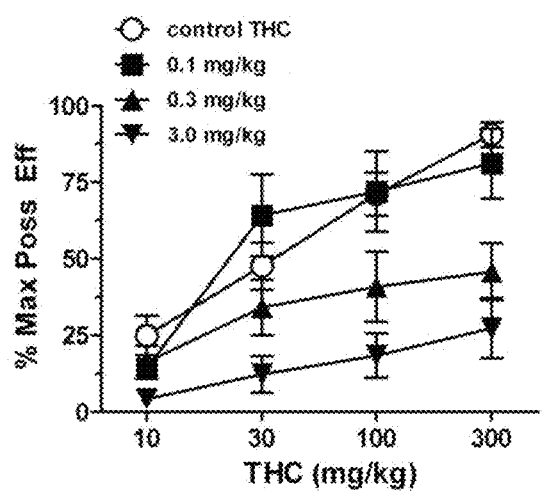
FIG. 4 illustrates the antinociceptive effects of the CB1 agonist $\Delta^9$-THC in mice, alone, or after 30-min pretreatment with Compound 1 (0.1, 0.3 and 3 mg/kg) (n=7-8 mice).

Antinociception is evaluated by measuring response latencies in the warm water tail-immersion (tail flick) assay using similar methods as described in *Arzneimittelforschung* 13:502-507 and *J Neurosci* 17:7157-7165; each herein incorporated by reference in its entirety. Response latencies are measured as the amount of time the animal takes to respond to the thermal stimuli. Male CD-1 mice (n=6, Charles River Breeding Laboratories, Wilmington, Mass., USA) weighing 30-35 g are group housed, 4 to a cage, in a temperature controlled (~20° C.), animal facility. Mice are habituated to the vivarium for at least 1 week prior to experiments with a light/dark cycle of 12:12 h (lights on at 7 a.m.) and are acclimatized to study procedures twice, prior to testing. Mice are given food and water ad libitum. Experimentally naïve mice are used for all procedures and tested during the light phase. All procedures are approved by The Animal Care and Use Committee of Northeastern University, Boston, Mass., USA. The "Principles of Animal Laboratory Care" (National Institute of Health 1996) is followed. For example, studies evaluated the pseudo-irreversible effects of the Compound 1 in mice using cumulative dosing procedures with THC. For example, FIG. 4 shows that a 30-min pretreatment of 0.3 mg/kg Compound 1 was able to produce a downward shift of the Δ$^9$-THC dose-effect function, and a dose of 3 mg/kg virtually eliminated the antinociceptive effects of up to 300 mg/kg Δ$^9$-THC. In comparison, Rimonabant, a CB1 inverse agonist produces surmountable rightward shift of Δ$^9$-THC dose-effect functions indicating that Compound 1 is behaving in an irreversible (or pseudo-irreversible) manner in vivo.

Example 9: Distribution and the Blood Brain Barrier

Mice (CD-1, weighing 25-30 g) are dosed intravenously or by oral gavage with 0.1-2 mg/kg of the compound dissolved in appropriate vehicle. Fifteen minutes post-injection or 30 and 60 minutes post-gavage, the animals are sacrificed humanely by decapitation followed by blood collection (~500 μL) and tissue dissection; samples are flash frozen with liquid nitrogen to prevent post-mortem degradation of the compounds or endogenous ligands. Tissues (plasma or brain) are extracted and analyzed using a Thermo-Finnigan Quantum Ultra triple quadrupole mass spectrometer with an Agilent 1100 HPLC front-end. Chromatographic separation is achieved using a Phenomenex Gemini column (2×50 mm, 5). Hardware consists of a Finnigan TSQ Quantum Ultra triple quad mass spectrometer with both an APCI and ESI source and an Agilent 1100 front end. The mass spectrometer with mobile phase consisting of 0.1% formic acid in water (A) and 0.1% formic acid in methanol (B). Similar to SR141716 (Rimonabant), Compound 1 and Compound 2 have a brain:plasma ratio of greater than 0.5.

In addition, where features or aspects of the disclosure are described in terms of Markush groups, those skilled in the art will recognize that the disclosure is also thereby described in terms of any individual member or subgroup of members of the Markush group.

Those skilled in the art will recognize, or be able to ascertain using no more than routine experimentation, many equivalents to specific embodiments of the disclosure described specifically herein. Such equivalents are intended to be encompassed in the scope of the disclosure.

All publications and patent applications referred to in this specification are herein incorporated by reference. Definitions that are contained in text incorporated by reference are excluded to the extent that they contradict definitions in this disclosure. Other embodiments are set forth in the following claims.

What is claimed is:

1. A compound of the Formula I:

V-V1-V2-R-W', wherein

V is ONO$_2$;
V1 is a straight chained hydrocarbon group containing 2 to 10 carbon atoms and a carbon-carbon triple bond group;
V2 is a phenyl group;
R is a heteroaromatic group selected from

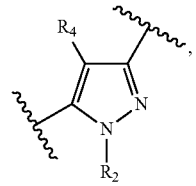

wherein R2 is phenyl, and
R4 is alkyl;
W' is -A-C'-B'-D wherein
  A is -C(=D1)-,
  C' is a direct bond,
  B' is —N(D2),
  D1 is O,
  D2 is selected from H and alkyl,
  D is selected from the group consisting of

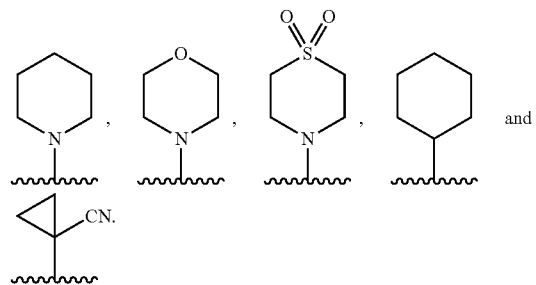

2. A compound of claim 1, wherein at least one atom in the compound is an unnatural isotope.

3. A compound selected from:
4-(4-(1-(2,4-dichlorophenyl)-4-methyl-3-(piperidin-1-ylcarbamoyl)-1H-pyrazol-5-yl)phenyl)but-3-yn-1-yl nitrate;
4-(4-(1-(2,4-dichlorophenyl)-4-methyl-3-(morpholinocarbamoyl)-1H-pyrazol-5-yl)phenyl)but-3-yn-1-yl nitrate;
5-(4-(1-(2,4-dichlorophenyl)-3-((1,1-dioxidothiomorpholino)carbamoyl)-4-methyl-1H-pyrazol-5-yl)phenyl)pent-4-yn-1-yl nitrate;
4-(4-(3-((1-cyanocyclopropyl)carbamoyl)-1-(2,4-dichlorophenyl)-4-methyl-1H-pyrazol-5-yl)phenyl)but-3-yn-1-yl nitrate;
5-(4-(1-(2,4-dichlorophenyl)-3-((1,1-dioxidothiomorpholino)carbamoyl)-4-methyl-1H-pyrazol-5-yl)phenyl)pent-4-yn-1-yl nitrate;
4-(4-(1-(2,4-dichlorophenyl)-3-((hexahydrocyclopenta[c]pyrrol-2(1H)-yl)carbamoyl)-4-methyl-1H-pyrazol-5-yl)phenyl)but-3-yn-1-yl nitrate;
4-(4-(1-(2-chloro-4-fluorophenyl)-4-methyl-3-(piperidin-1-ylcarbamoyl)-1H-pyrazol-5-yl)phenyl)but-3-yn-1-yl nitrate;

4-(4-(1-(2-chloro-4-fluorophenyl)-4-methyl-3-(morpholinocarbamoyl)-1H-pyrazol-5-yl)phenyl)but-3-yn-1-yl nitrate;

4-(4-(1-(2-chloro-4-fluorophenyl)-3-((1,1-dioxidothiomorpholino)carbamoyl)-4-methyl-1H-pyrazol-5-yl)phenyl)but-3-yn-1-yl nitrate; and 4-(4-(1-(2-chloro-4-fluorophenyl)-3-((1,1-dioxidothiomorpholino)carbamoyl)-4-methoxy-1H-pyrazol-5-yl)phenyl)but-3-yn-1-yl nitrate.

\* \* \* \* \*